US006303742B1

(12) United States Patent
Okada et al.

(10) Patent No.: US 6,303,742 B1
(45) Date of Patent: Oct. 16, 2001

(54) POLYIMIDE COMPOSITIONS

(75) Inventors: Kohji Okada; Hitoshi Nojiri, both of Otsu (JP)

(73) Assignee: Kanekafuchi Kagaku Kogyo Kabushiki Kaisha (JP)

( * ) Notice: Subject to any disclaimer, the term of this patent is extended or adjusted under 35 U.S.C. 154(b) by 0 days.

(21) Appl. No.: 09/424,925

(22) PCT Filed: Mar. 31, 1999

(86) PCT No.: PCT/JP99/01705

§ 371 Date: Dec. 1, 1999

§ 102(e) Date: Dec. 1, 1999

(87) PCT Pub. No.: WO99/51662

PCT Pub. Date: Oct. 14, 1999

(30) Foreign Application Priority Data

| Apr. 1, 1998 | (JP) | 10-088681 |
| May 20, 1998 | (JP) | 10-138758 |
| Jun. 4, 1998 | (JP) | 10-156388 |
| Jun. 4, 1998 | (JP) | 10-156411 |
| Jun. 4, 1998 | (JP) | 10-156426 |
| Jun. 5, 1998 | (JP) | 10-156990 |
| Jun. 5, 1998 | (JP) | 10-157056 |
| Jun. 10, 1998 | (JP) | 10-226294 |
| Jun. 18, 1998 | (JP) | 10-171521 |

(51) Int. Cl.[7] ................ C08G 73/100; C08G 9/28; C08L 77/00

(52) U.S. Cl. ............... 528/353; 528/125; 528/128; 528/170; 528/171; 528/172; 528/173; 528/174; 528/176; 528/179; 528/183; 528/185; 528/220; 528/229; 528/350; 524/600; 524/606

(58) Field of Search ................... 528/125, 128, 528/171, 170, 172, 173, 174, 220, 229, 353, 183, 185, 176, 179, 350; 524/600, 606

(56) References Cited

U.S. PATENT DOCUMENTS

| 4,595,745 | * | 6/1986 | Nakano et al. | 528/125 |
| 4,946,908 | * | 8/1990 | Chu et al. | 525/426 |
| 5,976,640 | * | 11/1999 | Yu et al. | 428/1.1 |
| 6,048,928 | * | 4/2000 | Yu et al. | 525/35 |

FOREIGN PATENT DOCUMENTS

| 2723099 | 2/1996 | (FR) . |
| 57-53454 | 3/1982 | (JP) . |

OTHER PUBLICATIONS

Berrada, M. et al., "Novel Negative–Type soluble Photosensitive Polyimides: Synthesis and Characterization", Chem., vol. 8, No. 5 (1996), pp. 1029–1034.

Berrada, M., et al., "Photoinduced Polymerization of Bisimides as Models for New Soluble side–Chain–Substituted Negative–Type Photosensitive Polyimides", chem.Mater., vol. 8, No. 5 (1996), pp. 1022–1028.

* cited by examiner

*Primary Examiner*—P. Hampton-Hightower
(74) *Attorney, Agent, or Firm*—Fitch, Even, Tabin & Flannery

(57) ABSTRACT

The present invention provides a novel polyimide composition which includes a cinnamoyl group or a derived cinnamoyl group and has photo-reactivity and heat-reactivity inherent to the cinnamoyl group. Further, a novel diamine and an acid dianhydride according to the present invention are materials mainly used for preparing a novel polyimide composition having the cinnamoyl group or the derived cinnamoyl group in a main chain or a side chain.

15 Claims, No Drawings

The present invention relates to novel polyimide compositions and methods for their production. More particularly, the invention relates to novel polyimide compositions which include a cinnamoyl group or a derived cinnamoyl group and have photo-reactivity and heat-reactivity which are inherent in the cinnamoyl group.

BACKGROUND ART OF THE INVENTION

Dimerization of cinnamic acid by ultraviolet radiation has been known for years. Therefore, it is conceivable that a useful photo-sensitive resin will be obtained by incorporating a cinnamoyl group into a polymer. Conventionally known as a polymer having a cinnamoyl group is polyvinyl cinnamate (polyvinyl having a cinnamoyl group) (Jpn. J. Appl. Phys., 31(1992), 2155, and J. Photopolymer Sci. and Tech. 8(1995), 257). The polyvinyl cinnamate is a useful photo-sensitive resin which becomes insoluble in a solvent when the cinnamoyl group is dimerized by light radiation (J. Appl. Polymer Sci., 2, 302(1959)), and used as a negative photo-sensitive resin.

However, the aforesaid polyvinyl cinnamate is poor in heat resistance and, hence, cannot be used in applications which require heat resistance.

Meanwhile, a reaction process is facilitated by first introducing a cinnamoyl group into a starting material of a polymer, i.e., a reactive monomer, and then polymerizing the monomer. However, no such reactive monomer is yet in existence.

Among a variety of organic polymers, polyimides and polyamides are particularly excellent resins which find wide applications in various fields ranging from the aerospace field to the electronic comunications field because of their superior heat resistance, and have been expected to be applicable to photo-sensitive resins.

In general, starting materials for an aromatic polyimide are an aromatic amine and an acid dianhydride, and starting materials for an aromatic polyamide are an aromatic amine and an aromatic dicarboxylic acid or an aromatic dicarboxylic acid chloride. An aromatic acid dianhydride having a cinnamoyl group has not been known yet.

The aromatic amine is generally obtained by reducing an aromatic nitro compound. For production of a polyimide or polyamide having a cinnamoyl group, an aromatic amine having the cinnamoyl group is first obtained by reduction of a nitro compound having the cinnamoyl group, and then polymerization is carried out to afford the polyimide or polyamide. However, processes for the reduction of the aromatic nitro compound into the aromatic amine currently suffer from the following drawbacks. Further, few amines which have the cinnamoyl group and are usable as monomers for photo-sensitive resin materials have been known, and neither polyimide nor polyamide exists which has the cinnamoyl group and is usable as a photo-sensitive resin.

Common processes for reducing an aromatic nitro compound into an aromatic amine include: (1) reduction with a metal or a metal salt; (2) reduction with hydrazine; (3) hydrogenation with a Pd-activated charcoal catalyst; and the like.

Examples of the process (1) include reduction with tin chloride in a hydrochloric acid solution (tin-hydrochloric acid system), reduction with iron sulfate followed by neutralization with ammonia (iron sulfate-ammonia system), and reduction with metal iron in a solution (Bechamp reduction).

In these processes, however, precipitation of metal salts results from neutralization upon completion of the reaction, so that a very troublesome operation is required in isolation of the aromatic amine. In addition, these processes suffer from a problem such that breakage of ester linkage may occur due to the reaction under acidic conditions or a Michael addition may occur due to the reaction under alkaline conditions.

Examples of the process (2) include hydrogenation with a Pd-activated charcoal catalyst, and hydrogenation with a Raney nickel catalyst.

Among these processes, the hydrogenation with the Pd-activated charcoal catalyst is not preferred because a side reaction such as a Michael addition or decomposition of a nitro compound may occur. One example of the hydrogenation with the Raney nickel catalyst is described in Heiv. Chim. Actra., 24, 209E (1941), in which aminocinnamic acid is synthesized from nitrocinnamic acid with the use of hydrazine in the presence of the Raney nickel catalyst. However, if this system is applied to reduction of a nitrocinnamic acid derivative instead of nitrocinnamic acid, a side reaction such as a Michael addition may proceed.

In the process (3), reduction is generally allowed to proceed with the use of a Pd-activated charcoal catalyst in an organic solvent under a hydrogen atmosphere. With the use of an ordinary Pd-activated charcoal, even a double bond of a cinnamoyl group may be reduced.

As described above, it is very difficult to optimize the conditions for the reduction of the nitro compound, so that few amines having the cinnamoyl group have been isolated.

In order to solve the aforesaid problems, the present invention is directed to provide a method for preparing a novel amine having a cinnamoyl group or a derived cinnamoyl group by optimizing conditions for reduction of a nitro compound, such a novel amine having been considered impossible to prepare.

It is an object of the present invention to provide a novel diamine or a novel acid dianhydride to provide a novel polyimide composition having a cinnamoyl group or a derived cinnamoyl group.

It is another object of the invention to provide a novel polyimide composition prepared from a novel diamine or a novel acid dianhydride having a cinnamoyl group or a derived cinnamoyl group.

It is further another object of the invention to provide a method for producing a novel diamine having a cinnamoyl group or a derived cinnamoyl group.

DISCLOSURE OF THE INVENTION

As a result of intensive studies to provide a novel polyimide composition having a cinnamoyl group or a derived cinnamoyl group and exhibiting photo-sensitivity as well as photo-reactivity, the inventors of the present invention have attained the present invention.

A novel polyimide composition of the present invention comprises a cinnamoyl group incorporated in a main chain or a side chain.

A novel polyimide composition of the present invention comprises a monomer unit of the general formula (1) in a proportion of not smaller than 1% by weight:

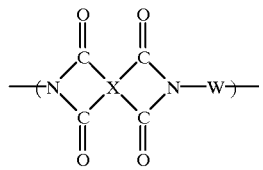
(1)

wherein X is a tetravalent organic group, and W is a divalent organic group selected from divalent organic groups represented by the formulae (1-a), (1-b), (1-c), (1-d), (1-e) and (1-f):

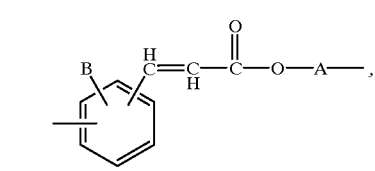
(1-a)

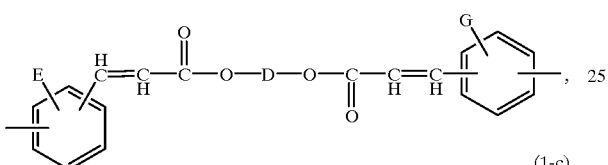
(1-b)

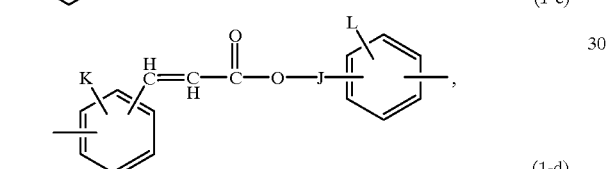
(1-c)

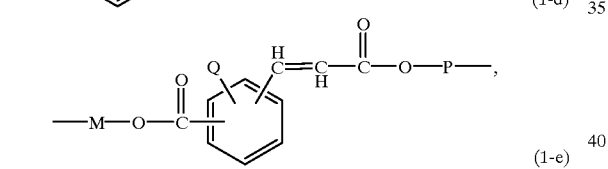
(1-d)

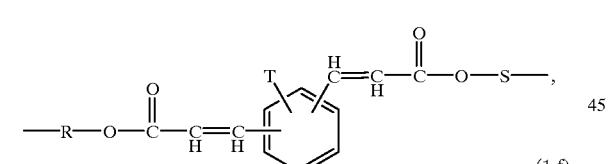
(1-e)

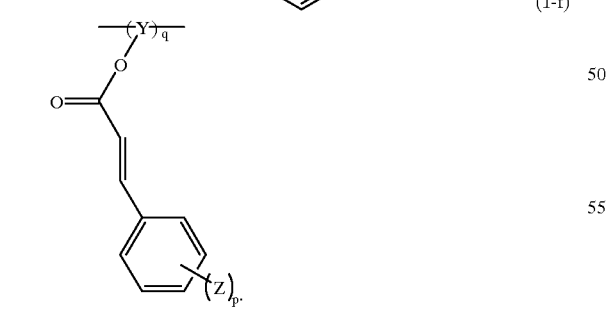
(1-f)

In the novel polyimide composition of the invention, X in the general formula (1) represents one or two or more kinds of tetravalent organic groups which each comprise one to three aromatic rings or an aliphatic ring.

In the novel polyimide composition of the invention, B in the formula (1-a) represents a group selected from H, $CH_3$, F, Cl, Br and $CH_3O$—, and A is a divalent organic group selected from the following groups:

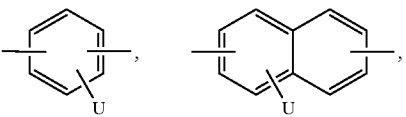
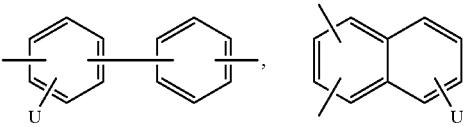
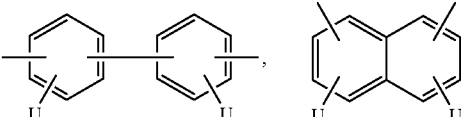
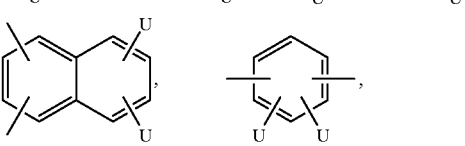
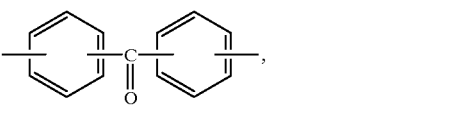
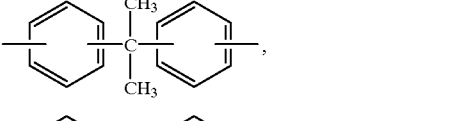
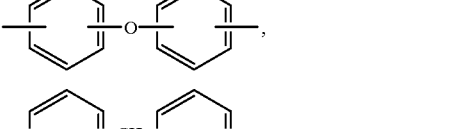
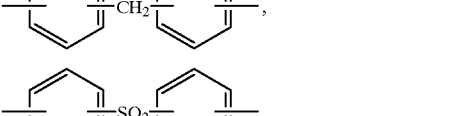
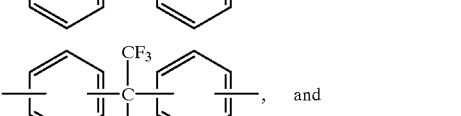
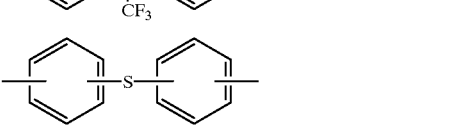
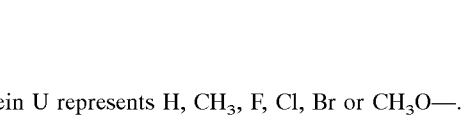
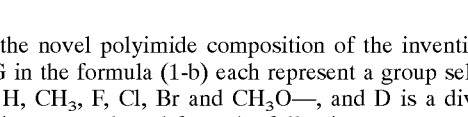, and
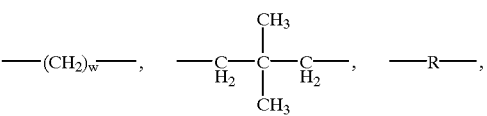

wherein U represents H, $CH_3$, F, Cl, Br or $CH_3O$—.

In the novel polyimide composition of the invention, E and G in the formula (1-b) each represent a group selected from H, $CH_3$, F, Cl, Br and $CH_3O$—, and D is a divalent organic group selected from the following groups:

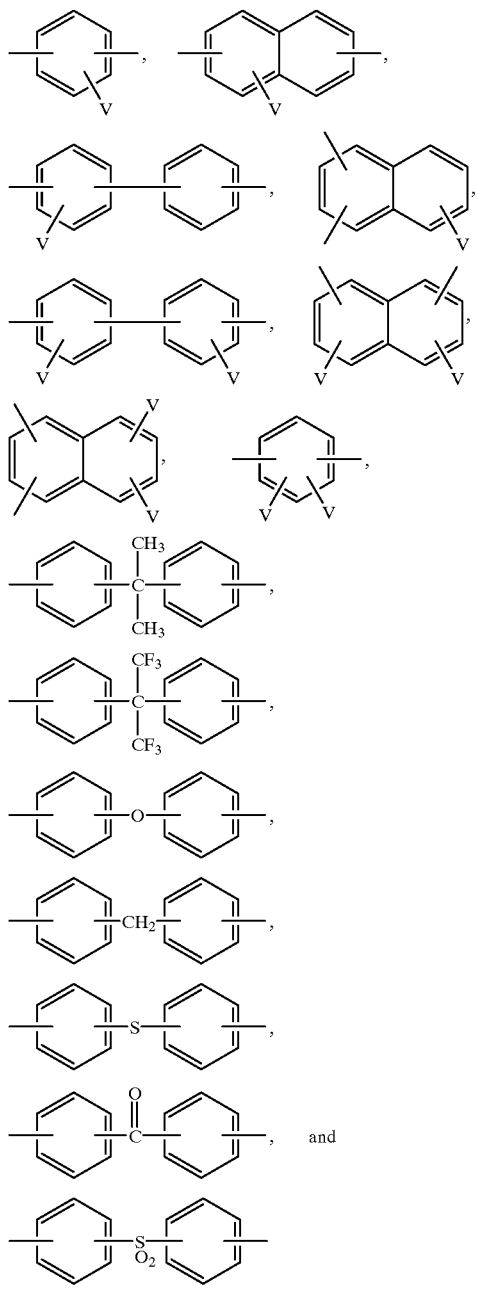

wherein w is an integer from 1 to 40, and V represents H, CH₃F, Cl, Br or CH₃O—.

In the novel polyimide composition of the invention, K and L in the formula (1-c) each represent H, CH₃, F, Cl, Br or CH₃O—, and J represents —CH₂—, —(CH₂)$_m$—O— or —(CH₂)$_n$—OCO—, wherein m=1 to 15 and n=1 to 15.

In the novel polyimide composition of the invention, M and P in the formula (1-d), which may be the same or different, each represent a divalent organic group selected from the following groups:

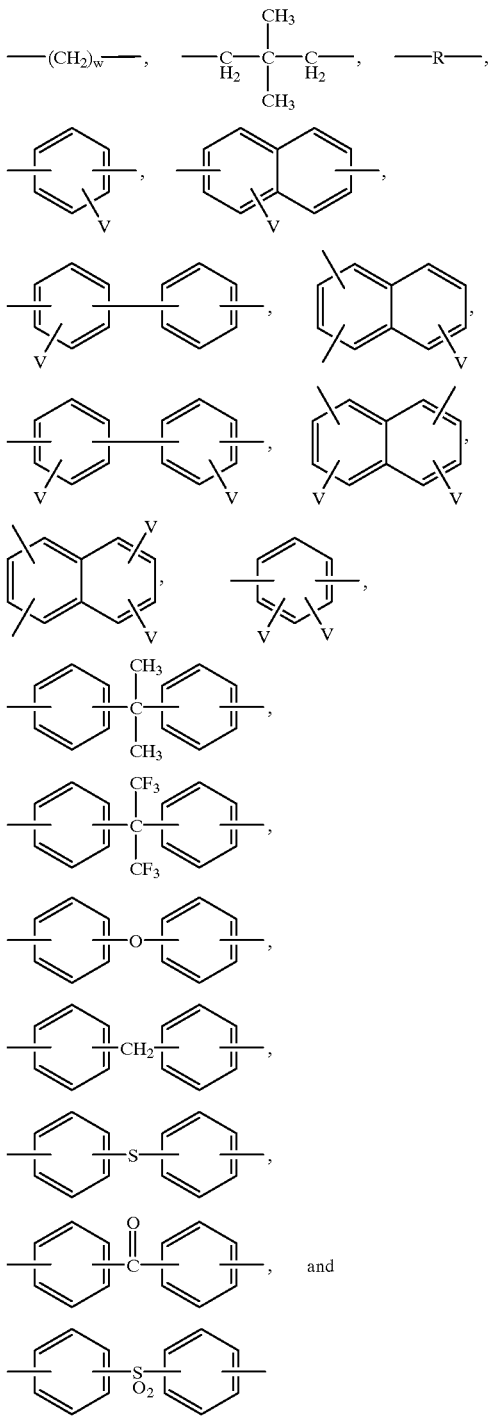

wherein w is an integer from 1 to 40, and Q and V each represent H, CH₃, F, Cl, Br or CH₃O—.

In the novel polyimide composition of the invention, T in the formula (1-e) represents H, CH₃, F, Cl, Br or CH₃O—, and R and S, which may be the same or different, each represent a divalent organic group selected from the following groups:

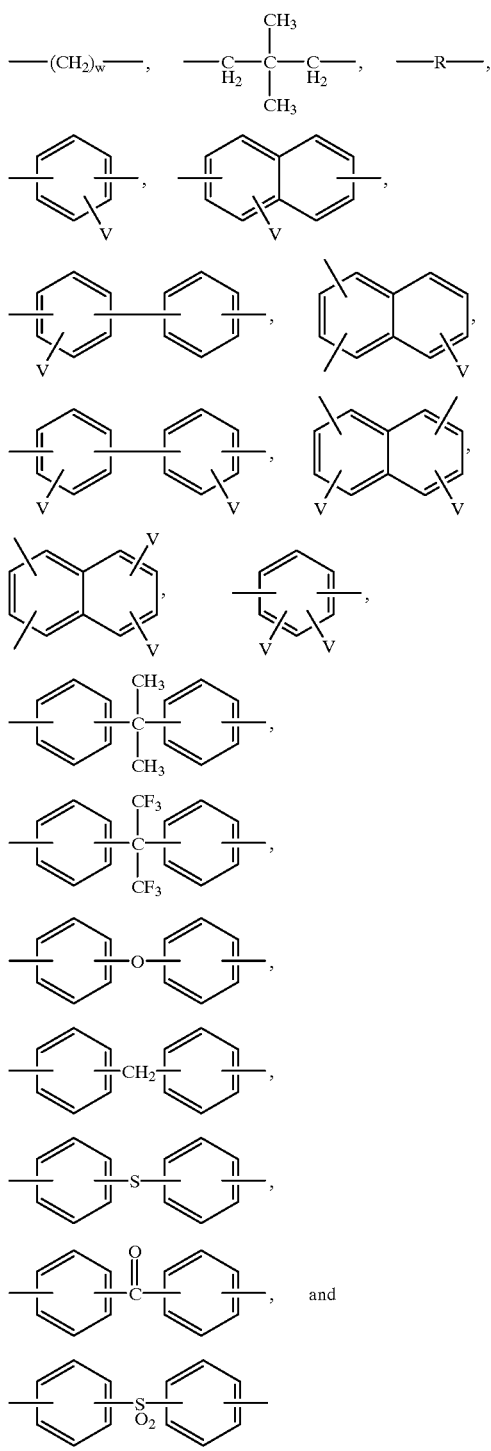

wherein w is an integer from 1 to 40, and Q and V each represent H, CH₃, F, Cl, Br or CH₃O—.

In the novel polyimide composition, Z in the formula (1-f) represents H, CH₃, F, Cl, Br or CH₃O—, p=1 to 3, q=1 to 3, and Y represents a trivalent organic group selected from the following groups:

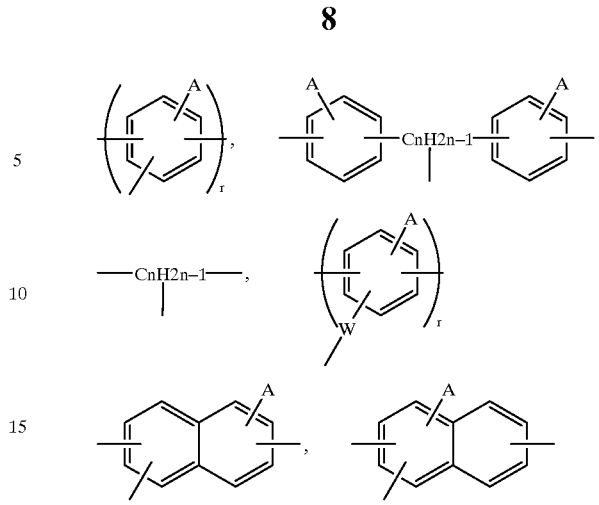

wherein A represents H, CH₃, F, Cl, Br or CH₃O—, r=1 to 3, n=1 to 20, W represents a divalent organic group selected from —CH₂—, —(CH₂)m—O— (wherein m=1 to 15) and —(CH₂)$_k$—OCO—(wherein k=1 to 20 (k≠2)).

Another novel polyimide composition of the present invention comprises a monomer unit of the general formula (2) in a proportion of not smaller than 1% by weight:

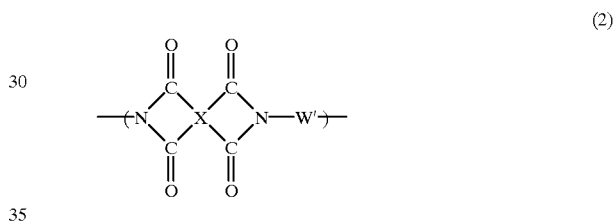

(2)

wherein X' is a group represented by one of the following formulae (2-a) and (2-b):

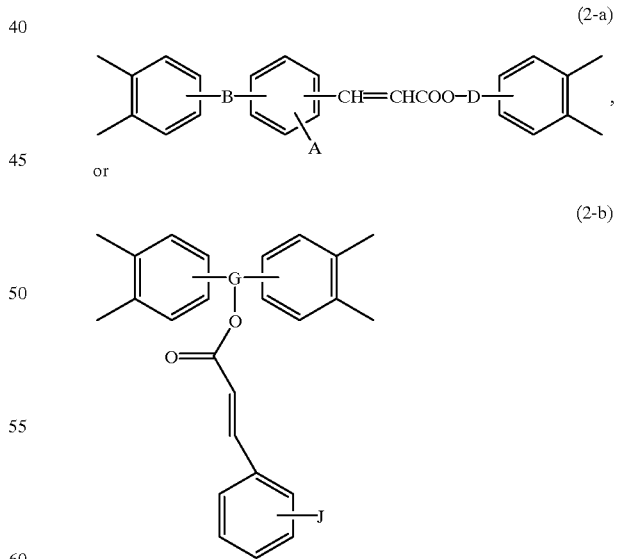

wherein W' represents a divalent organic group, B and D each represent a divalent organic group, and A represents H, CH₃, F, Cl, Br or CH₃O—, and G in formula (2-b) represents a trivalent organic group.

In the novel polyimide composition of the invention, B in the formula (2-a) represents a divalent organic group selected from —COO—, —OCO—, —O—, —O—E—O—, —COO—E—OCO—, —O—E—OCO—, —O—E—COO— and —OOCCH=CH— wherein E represents —$C_mH_{2m}$— (wherein m represents an integer from 1 to 20), a benzene ring, a naphthalene ring or a biphenyl.

In the novel polyimide composition of the invention, D in the formula (2-a) represents a single bond (—) or a divalent organic group selected from —F—OCO— and —F—O— wherein F represents —$CH_mH_{2m}$— (wherein m represents an integer from 1 to 20), a benzene ring or a naphthalene ring.

In the novel polyimide composition of the invention, such as in formula (2-b) J represents H, $CH_3$, F, Cl, Br or $CH_3O$—.

In the novel polyimide composition of the invention, G in the formula (2-b) represents one of the following groups:

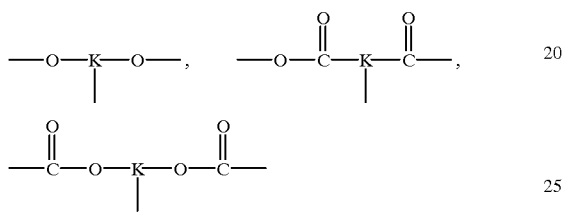

wherein K represents —$CH_nH_{2n-1}$— (wherein n represents an integer from 1 to 20), a benzene ring, a naphthalene ring or a biphenyl.

A novel diamine of the present invention is a diamine represented by the general formula (3):

(3)

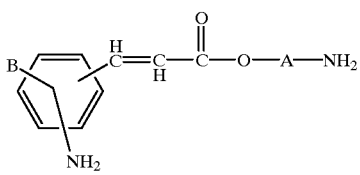

wherein A represents a divalent organic group selected from the following groups:

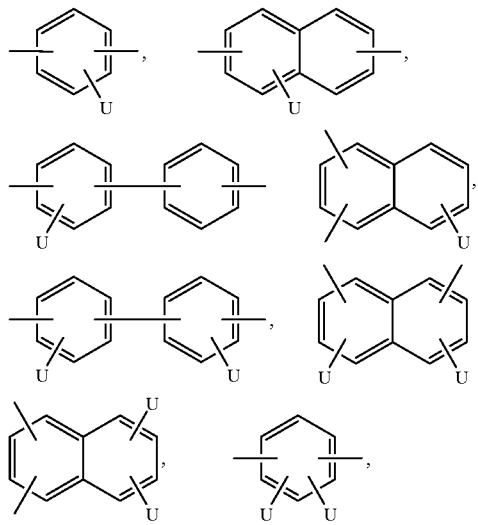

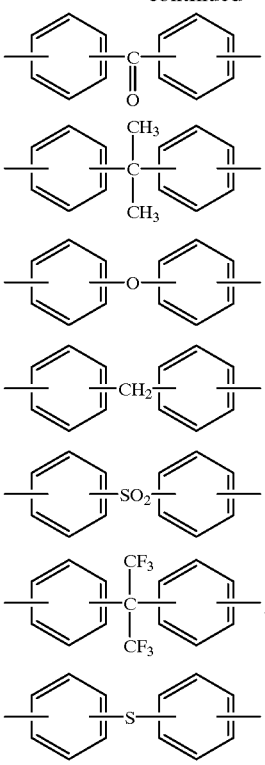

wherein U represents H, $CH_3$, F, Cl, Br or $CH_3O$—.

Another novel diamine of the present invention is a diamine represented by the general formula (4):

(4)

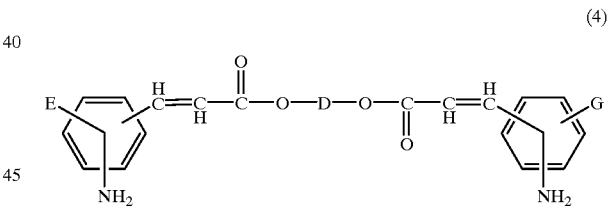

wherein D represents a diva-lent organic group selected from the following groups:

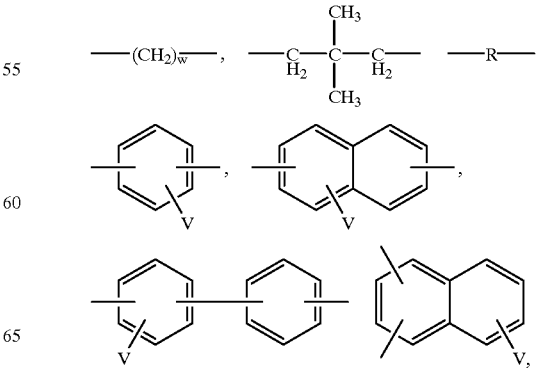

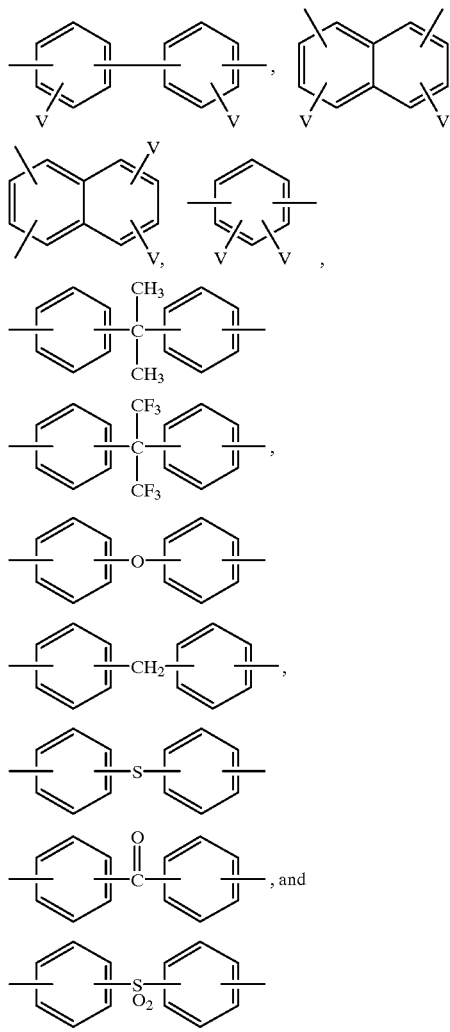

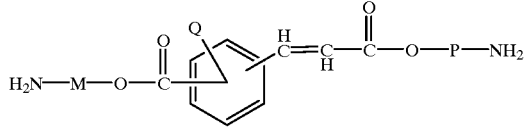

wherein w represents an integer from 1 to 40, and V represents H, CH₃, F, Cl, Br or CH₃O—.

Further another diamine of the present invention is a diamine represented by the general formula (5):

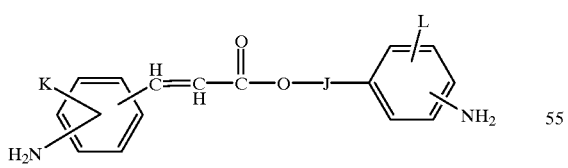

wherein K and L each represent a group selected from H, CH₃, F, Cl, Br and CH₃O—, and J represents a divalent organic group selected from —CH₂—, —(CH₂)$_m$—O— (wherein m=1 to 15) and —(CH₂)$_n$—OCO— (wherein n=1 to 15).

Still another diamine of the present invention is a diamine represented by the general formula (6):

wherein M and P, which may be the same or different, each represent a divalent organic group selected from the following groups:

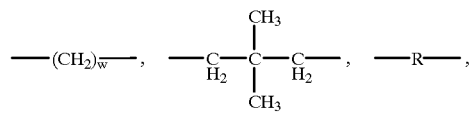

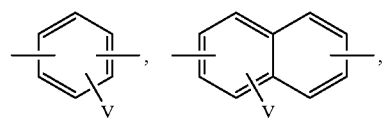

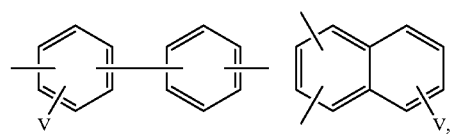

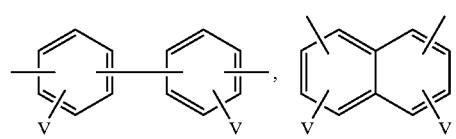

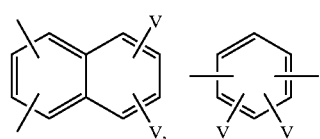

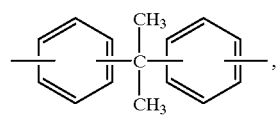

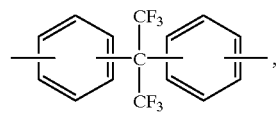

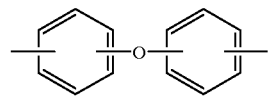

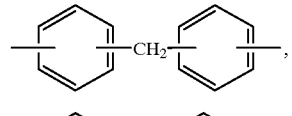

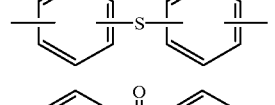

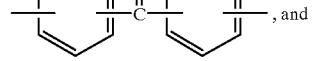

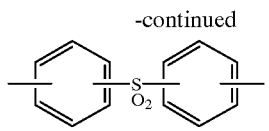

wherein w represents an integer from 1 to 40, and Q and V each represent H, CH$_3$, F, Cl, Br or CH$_3$O—.

Further another diamine of the present invention is a diamine represented by the general formula (7):

(7)

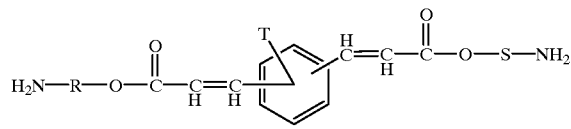

wherein R and S, which may be the same or different, each represent a divalent organic group selected from the following groups:

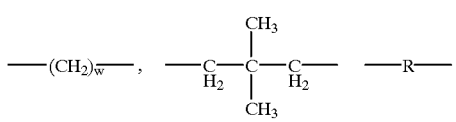

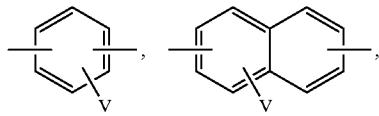

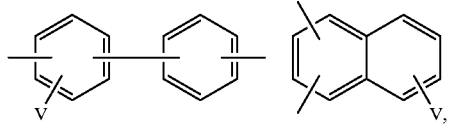

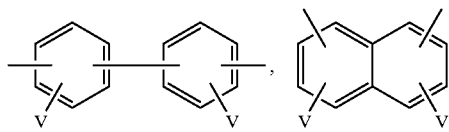

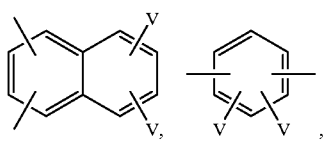

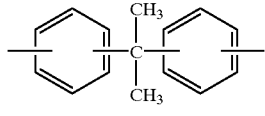

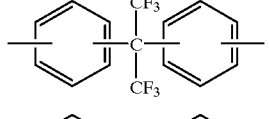

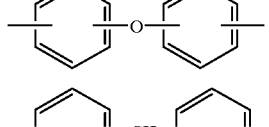

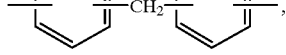

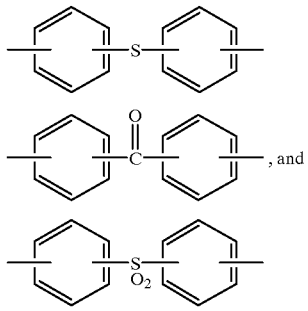

wherein w represents an integer from 1 to 40, and T and V each represent H, CH$_3$, F, Cl, Br or CH$_3$O—.

Still another diamine of the present invention is a diamine represented by the general formula (8):

(8)

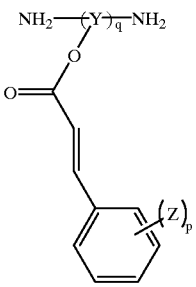

wherein Z represents H, CH$_3$, F. Cl, Br or CH$_3$O—, p=1–3, q=1–3, and Y represents a trivalent organic group selected from the following groups:

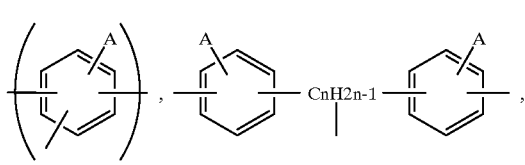

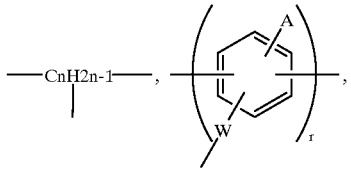

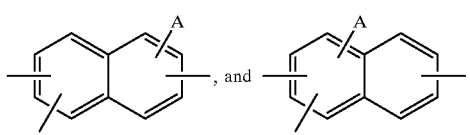

wherein A represents H, CH$_3$, F, Cl, Br or CH$_3$O—, r=1–3, n=1–2, W represents a divalent organic group selected from among —CH$_2$—, —(CH$_2$)$_m$—O—, and —(CH$_2$)$_k$OCO—, wherein m=1–15, k=1–20 (k≠2).

A novel acid dianhydride of the present invention is an acid dianhydride represented by the following general formula (9):

(9)

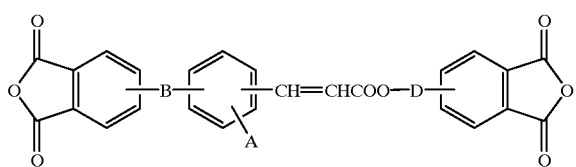

wherein B and D each represent a divalent organic group, and A represents H, CH$_3$, F, Cl, Br or CH$_3$O—.

In the novel acid dianhydride of the invention, B in the general formula (9) represents a divalent organic group selected from —COO—, —OCO—, —O—, —O—E—O, —COO—E—OCO—, —O—E—OCO—, —O—E—COO— and —OOCCH=CH— wherein E represents —C$_m$H$_{2m}$— (wherein m represents an integer from 1 to 20), a benzene ring, a naphthalene ring, or a biphenyl.

In the novel acid dianhydride of the invention, D in the general formula (9) represents a single bond (—) or a divalent organic group selected from —F—OCO— and —F—O— wherein F represents an integer from 1 to 20, represents —C$_m$H$_{2m}$— (wherein m represents an integer from 1 to 20), a benzene ring or a naphthalene ring.

Another novel acid dianhydride of the present invention is an acid dianhydride represented by the general formula (10):

(10)

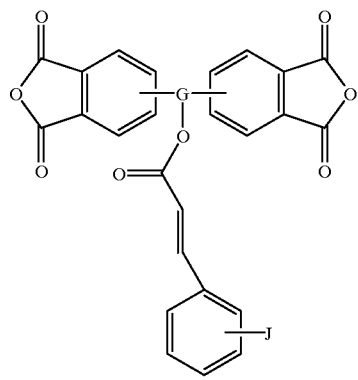

wherein G represents a trivalent organic group, and J represents H, CH$_3$, F, Cl, Br or CH$_3$O—.

In the novel acid dianhydride of the invention, G in the general formula (10) represents one of the following groups:

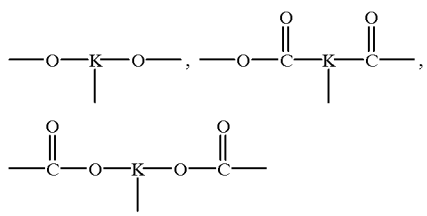

wherein K represents C$_n$H$_{2n-1}$ (wherein n represents an integer from 1 to 20), a benzene ring, a naphthalene ring or a biphenyl.

An aromatic amine preparation method according to the present invention is based on hydrogenation with a Pt-carbon-black catalyst.

Another aromatic amine preparation method according to the present invention is based on hydrogenation with a Pt-activated charcoal catalyst whose selective activity for a nitro group is enhanced by a metal selected from Fe, Na, Cu and Ni.

DESCRIPTION OF THE PREFERRED EMBODIMENTS

Novel polyimide compositions according to the present invention are characterized by a cinnamoyl group or a derived cinnamoyl group incorporated therein and by photo-reactivity and heat-reactivity which are inherent in the cinnamoyl group. The novel diamines and acid dianhydrides according to the present invention are materials to be mainly used for production of the aforesaid novel polyimide compositions having the cinnamoyl group, and each have the cinnamoyl group or the derived cinnamoyl group incorporated in a main chain or side chain thereof.

Although exemplary structures of the novel polyamide compositions of the present invention will be described by way of an embodiment, the structures of the polyimide compositions are not particularly limited as long as the cinnamoyl group is incorporated therein.

Examples of the polyimide compositions of the present invention will hereinafter be described, the structures of which are not particularly limited as long as the cinnamoyl group is incorporated in a main chain or a side chain.

A polyimide composition having a cinnamoyl group incorporated in a diamine residue comprises a monomer unit of the general formula (1) in a proportion of not smaller than 1% by weight:

(1)

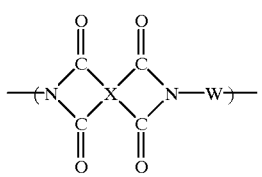

wherein X is a tetravalent organic group, and W is a divalent organic group selected from divalent organic groups represented by the formulae (1-a), (1-b), (1-c), (1-d), (1-e) and (1-f):

(1-a)

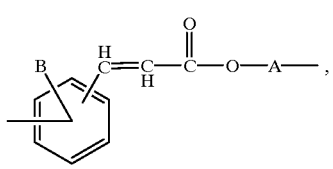

(1-b)

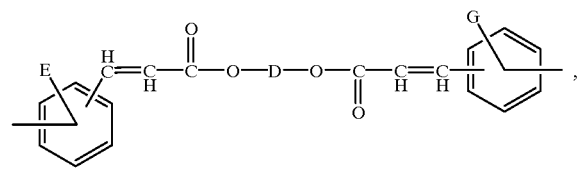

-continued (1-c)

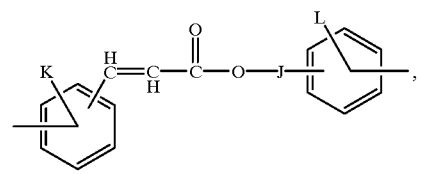

(1-d)

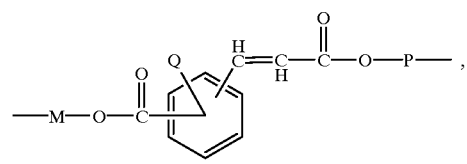

(1-e)

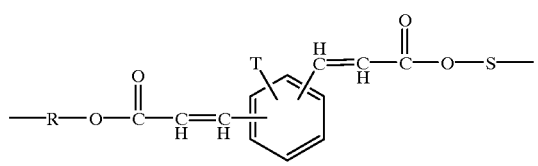

(1-f)

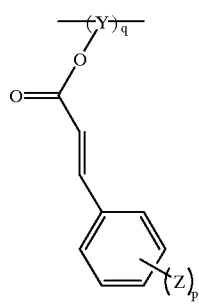

A polyimide composition including a cinnamoyl group in an acid dianhydride residue comprises a monomer unit of the general formula (2) in a proportion of not smaller than 1% by weight:

(2)

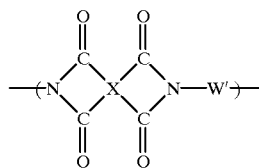

wherein X' is a group represented by one of the formulae (2-a) and (2-b):

(2-a)

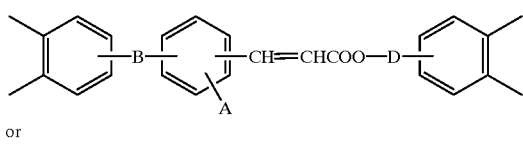

or

-continued (2-b)

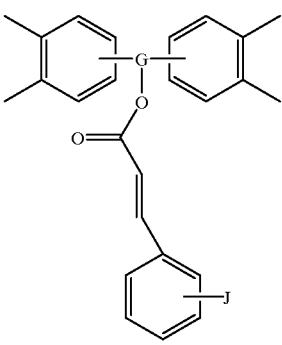

and W' represents a divalent organic group.

An explanation will hereinafter be given to the polyimide compositions each including a cinnamoyl group in accordance with the present invention and to production methods therefor.

Exemplary production methods for a polyimide having a cinnamoyl group in a diamine residue thereof include: (1) a method in which a diamine having a cinnamoyl group is first synthesized and then reacted with a given acid dianhydride for preparation of a polyamic acid, which is dehydrated for ring closure for preparation of the polyimide; and (2) a method in which a diol-terminated polyimide oligomer is reacted with a dicarboxylic acid or a diacid chloride to form ester linkage for polymerization, thereby preparing the polyimide composition.

An explanation will first be given to the polyimide composition production method (1) using a diamine having a cinnamoyl group.

The novel polyimide composition wherein W in the general formula (1) is represented by the formula (1-a), more specifically, which comprises a monomer unit represented by the following formula:

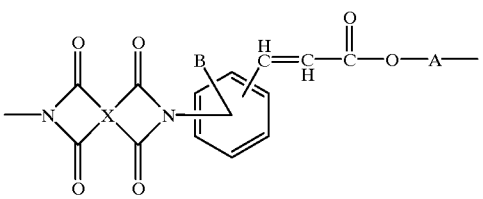

is employed as an example for explanation of a specific polyimide composition production method according to the present invention.

A diamine as a material for the novel polyimide composition wherein W in the general formula (1) is represented by the formula (1-a) is represented by the general formula (3):

(3)

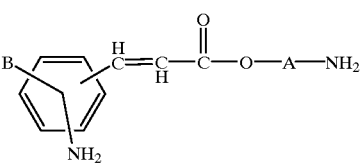

wherein B represents H, $CH_3$, F, Cl, Br or $CH_3O-$, and A represents a divalent organic group.

The diamine can be obtained by reacting a cinnamic acid derivative or a cinnamoyl chloride derivative with a nitro compound having a hydroxyl group to afford a dinitro compound and then reducing the dinitro compound.

More specifically, the cinnamic acid derivative is represented by the formula (1-2):

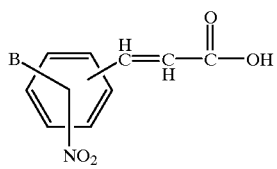

(1-2)

wherein B represents H, $CH_3$, F, Cl, Br or $CH_3O$—.

The cinnamoyl chloride derivative is represented by the formula (1-3):

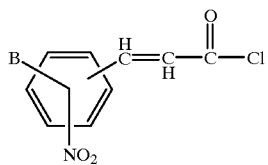

(1-3)

wherein B represents H, $CH_3$, F, Cl, Br or $CH_3O$—.

The nitro compound having a hydroxyl group is represented by the formula (1-4):

$O_2N$—A—OH (1-4)

wherein A represents a divalent organic group.

These compounds are reacted with each other to afford a dinitro compound represented by the formula (1-5):

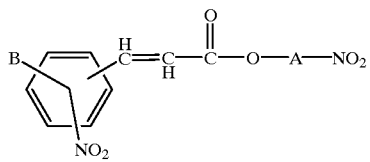

(1-5)

wherein B represents H, $CH_3$, F, Cl, Br or $CH_3O$—.

In the formulae (1-4) and (1-5), A is a divalent organic group, which is not particularly limited but examples thereof include the following groups:

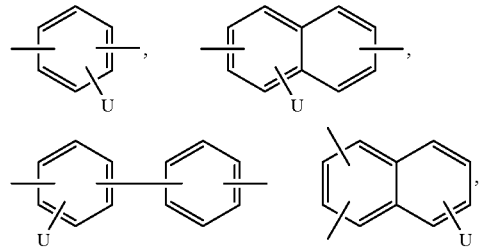

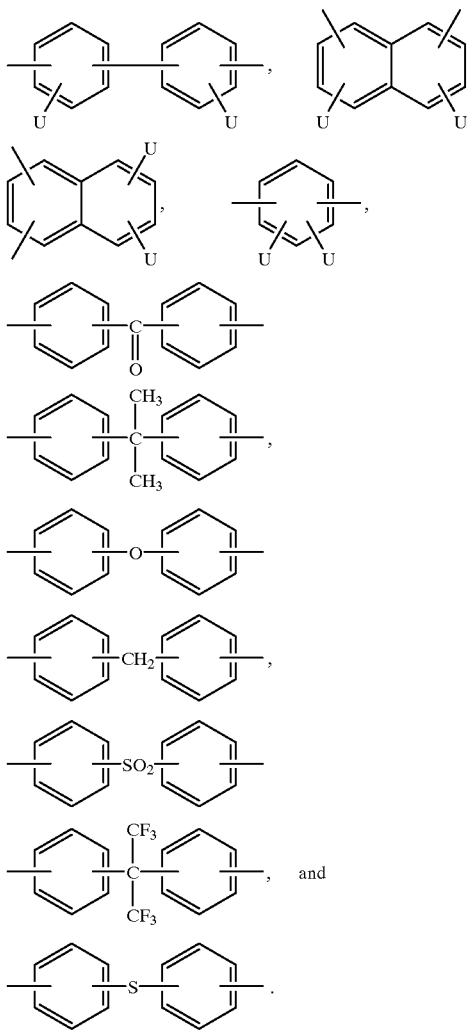

Next, conditions for the reduction of the dinitro compound will be described.

Exemplary methods for reduction of an aromatic nitro compound into an aromatic amine include: (1) reduction with a metal or a metal salt; (2) reduction with hydrazine; and (3) hydrogenation with the use of a Pd-activated charcoal catalyst. Basically, any of these reduction methods can be employed for the preparation of the aromatic amine according to the present invention.

However, since the aromatic nitro compound to be employed in the invention has a double bond attributed to the cinnamoyl group, selection of severe reduction conditions may result in reduction of the double bond. Further, reduction under strong acidic conditions may result in breakage of ester linkage, and reduction under alkaline conditions may result in a Michael addition. Therefore, the reduction conditions should be optimized.

In the present invention, the dinitro compound is subjected to the Bechamp reduction or hydrogen reduction with the use of a Pt-carbon black catalyst or a Pt-activated charcoal catalyst having a selective activity enhanced by iron or the like to afford a compound of the general formula (3) in a high yield:

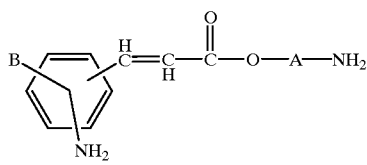 (3)

wherein A is a divalent organic group, and B represents H, CH$_3$, F, Cl, Br or CH$_3$O—.

In the present invention, the "Pt-activated charcoal" is a catalyst comprising activated charcoal and platinum carried thereon, and the "Pt-carbon black" is a catalyst comprising carbon black and platinum carried thereon.

In the reduction method suitable for the reduction of the dinitro compound, it is particularly preferred to employ a reduction catalyst comprising an activated charcoal carrier, and Pt carried thereon, more effectively a carbon black carrier and Pt carried thereon. The inventors have newly found that the reaction selectivity for a nitro group is remarkably enhanced by employing the Pt-carbon black catalyst or the selectivity-enhanced Pt-activated charcoal catalyst for the hydrogen reduction of the nitro compound having the cinnamoyl group in an organic solvent. The inventors have successfully obtained the intended novel amine having the cinnamoyl group from the nitro compound in a very high yield with the use of the reduction catalyst.

The Pt-carbon black catalyst is preferred, because the nitro group is preferentially reduced with the use of the Pt-carbon black catalyst with virtually no double bond reduction in the reduction system to afford the intended diamine in a high yield. A Pt-carbon black catalyst containing a metal such as Fe, Na, Cu or Ni also provides an excellent effect in the reaction selectivity for the nitro group. A Pt-carbon black catalyst containing Fe is preferred because it ensures a particularly high reaction selectivity.

The activated charcoal, though offering a lower reaction selectivity than the carbon black, may be used as the carrier. In this case, a Pt-activated charcoal catalyst containing Fe, Na or the like is preferred because it provides a further excellent effect in the reaction selectivity for the nitro group.

In another reduction method, a Pd-activated charcoal catalyst may be employed. The Pd-activated charcoal catalyst for the reduction provides a high reaction activity to reduce the carbon-carbon double bond in the cinnamoyl group, so that a catalyst poison such as sulfur, sulfur dioxide or carbon monoxide may be added to the catalyst to ensure a reaction selectivity for the nitro group. Thus, the novel diamine according to the invention can be prepared. The term "catalyst poison" herein means a substance which is irreversibly adsorbed on active sites of the catalyst to deactivate the function as the catalyst.

Exemplary methods for hydrogenation include: a method in which hydrogen gas is directly blown into an organic solvent; a method in which the reaction is allowed to proceed at an atmospheric pressure under a hydrogen atmosphere; and a method in which the reaction is allowed to proceed in a pressure-proof reaction vessel such as an autoclave in which hydrogen gas is filled under applying pressure.

The reaction is preferably allowed to proceed at a temperature ranging from a room temperature to approximately 120° C. If the reaction temperature is not lower than 180° C., the breakage of the double bond of the cinnamoyl group may result. Therefore, it is necessary to carry out the reaction at a temperature lower than 180° C. A reaction temperature lower than a room temperature is not preferred from an industrial viewpoint, because a longer reaction time is required though the reaction may proceed at such a temperature.

The Pt-carbon black or Pt-activated charcoal catalyst contains platinum in a concentration of approximately 0.1 to 40% by weight, and provides a catalytic effect if the platinum concentration is not lower than 0.1%. The reaction rate tends to increase as the platinum concentration becomes higher. Since platinum is a precious metal, the catalyst to be used preferably has a platinum concentration of about 1 to 20%. The Pt-carbon black or Pt-activated charcoal catalyst may be used in a dry state or in a moistened state and, in either state, provides the same catalytic effect. The use of the catalyst in the moistened state is preferred from an industrial viewpoint, because handling of the catalyst is easy without scattering of particles of the catalyst.

The solvent to be used for the reduction is not particularly limited as long as the solvent is capable of dissolving the diamine and the dinitro compound therein and does not hinder the reaction. Examples of the solvent includes alcohols, aromatic solvents such as dioxane, toluene and xylene, sulfoxide solvents such as dimethyl sulfoxide and diethyl sulfoxide, formamide solvents such as N,N-dimethylformamide and N,N-diethylformamide, acetamide solvents such as N,N-dimethylacetamide and N,N-diethylacetamide, pyrrolidone solvents such as N-methyl-2-pyrrolidone and N-vinyl-2-pyrrolidone, phenol solvents such as phenol, o-, m- or p-cresol, xylenol, halogenated phenols and catechol, hexamethylphosphoramide, γ-butyrolactone, and any other solvents which are capable of dissolving the diamine and the dinitro compound and do not hinder the reaction.

One of the reduction methods suitable for the reduction of the dinitro compound is the Bechamp reduction method. According to this method, Fe powder is added to the dinitro compound in a solvent, and the resulting mixture is heated at a temperature not higher than 130° C. for the reduction. Any of the solvents described above may be used as the solvent in this method. Particularly, acetic acid, alcohols, dioxane and the like are preferred.

The novel amine having the cinnamoyl group can be prepared in a very high yield with the use of the reduction catalyst having a high selective activity for the nitro group by any of the aforesaid methods. Since the novel amine according to the invention has the cinnamoyl group, the cinnamoyl group can be introduced into polymers such as polyamides and polyimides having superior properties by employing the amine as a starting material. Thus, these polymers will find wider applications as thermosetting resins and photo-sensitive reins. Further, the amine can be obtained at a high purity and in a high yield, so that isolation and purification steps can be omitted. This is economically advantageous, because the polyimide/polyamide production step can directly follow the amine preparation step.

An explanation will next be given to a method for synthesizing a polyimide represented by the general formula (1) from the diamine obtained in the aforesaid manner.

The diamine of the general formula (3) obtained in the aforesaid manner and another kind of diamine are reacted with an acid dianhydride in an organic polar solvent to afford a polyamic acid.

Examples of the organic polar solvent to be used for the reaction for the preparation of the polyamic acid include sulfoxide solvents such as dimethyl sulfoxide and diethyl sulfoxide, formamide solvents such as N,N-dimethylformamide and N,N-diethylformamide, acetamide solvents such as N,N-dimethylacetamide and N,N-diethylacetamide, pyrrolidone solvents such as N-methyl-2-pyrrolidone and N-vinyl-2-pyrrolidone, phenol solvents such as phenol, o-, m- or p-cresol, xylenol, halogenated phenols and catechol, hexamethylphosphoramide, and γ-butyrolactone. These are preferably used either alone or in combination. Some aromatic solvents such as xylene and toluene may be used.

The acid dianhydride to be used in the present invention is not particularly limited, but examples thereof include: aliphatic or alicyclic tetracarboxylic dianhydrides such as butanetetracarboxylic dianhydride, 1,2,3,4-cyclobutanetetracarboxylic dianhydride, 1,3-dimethyl-1,2,3,4-cyclobutanetetracarboxylic acid, 1,2,3,4-cyclopentanetetracarboxylic dianhydride, 2,3,5-tricarboxycyclopentylacetic dianhydride, 3,5,6-tricarboxynorbornane-2-acetic dianhydride, 2,3,4,5-tetrahydrofurantetracarboxylic dianhydride, 5-(2,5-dioxotetrahydrofural)-3-methyl-3-cyclohexene-1,2-dicarboxylic dianhydride and bicyclo[2,2,2]-oct-7-ene-2,3,5,6-tetracarboxylic dianhydride; aromatic tetracarboxylic dianhydrides such as pyromellitic dianhydride, 3,3',4,4'-benzophenonetetracarboxylic dianhydride, 3,3',4,4'-biphenylsulfonetetracarboxylic dianhydride, 1,4,5,8-naphthalenetetracarboxylic dianhydride, 2,3,6,7-naphthalenetetracarboxylic dianhydride, 3,3',4,4'-biphenylethertetracarboxylic dianhydride, 3,3',4,4'-dimethyldiphenylsilanetetracarboxylic dianhydride, 3,3',4,4'-tetraphenylsilanetetracarboxylic dianhydride, 1,2,3,4-furantetracarboxylic dianhydride, 4,4'-bis(3,4-dicarboxyphenoxy)diphenyl sulfide dianhydride, 4,4'-bis(3,4-dicarboxyphenoxy)diphenyl sulfone dianhydride, 4,4'-bis(3,4-dicarboxyphenoxy)diphenylpropane dianhydride, 3,3',4,4'-perfluoroisopropylidenediphthalic dianhydride, 3,3',4,4'-biphenyltetracarboxylic dianhydride, bis(phthalic acid) phenylphosphine oxide dianhydride, p-phenylene-bis(triphenylphthalic acid) dianhydride, m-phenylene-bis(triphenylphthalic acid) dianhydride, bis(triphenylphthalic acid)-4,4'-diphenyl ether dianhydride, bis(triphenylphthalic acid)-4,4'-diphenylmethane dianhydride; aliphatic tetracarboxylic anhydrides having aromatic ring such as 1,3,3a,4,5,9b-hexahydro-2,5-dioxo-3-furanyl)-naphtho[1,2-c]furan-1,3-dione, 1,3,3a,4,5,9b-hexahydro-5-methyl-5-(tetrahydro-2,5-dioxo-3-furanyl)-naphtho[1,2-c]furan-1,3-dione, 1,3,3a,4,5,9b-hexahydro-8-methyl-5-(tetrahydro-2,5-dioxo-3-furanyl)-naphtho[1,2-c]furan-1,3-dione, compounds represented by the following general formula (11):

(11)

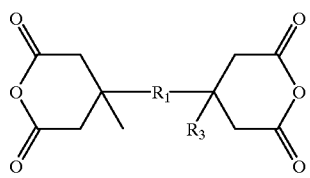

(wherein R1 represents a divalent organic group having aromatic ring, and R2 and R3 each represent a hydrogen atom or an alkyl group), and compounds represented by the following general formula (12):

(12)

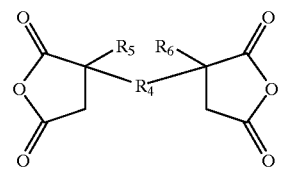

wherein R4 represents a divalent organic group having aromatic ring, and R5 and R6 each represent a hydrogen atom or an alkyl group. These tetracarboxylic dianhydrides may be used either alone or in combination of two or more.

Any of various diamines may be used in addition to the aforesaid diamine having the cinnamoyl group for the production of the polyimide composition of the present invention. The diamine is not particularly limited, but examples thereof include: aromatic diamines such as p-phenylenediamine, m-phenylenediamine, 4,4'-diaminodiphenylmethane, 4,4'-diaminodiphenylethane, 4,4'-diaminodiphenyl ether, 4,4'-diaminodiphenyl sulfide, 4,4'-diaminodiphenyl sulfone, 1,5-diaminonaphthalene, 3,3'-dimethyl-4,4'-diaminobiphenyl, 5-amino-1-(4'-aminophenyl)-1,3,3-trimethylindan, 6-amino-1-(4'-aminophenyl)-1,3,3-trimethylindan, 4,4'-diaminobenzanilide, 3,5-diamino-3'-trifluoromethylbenzanilide, 3,5-diamino-4'-trifluoromethylbenzanilide, 3,4'-diaminodiphenyl ether, 2,7-diaminofluorene, 2,2'-bis(4-aminophenyl) hexafluoropropane, 4,4'-methylene-bis(2-chloroaniline), 2,2',5,5'-tetrachloro-4,4'-diaminobiphenyl, 2,2'-dichloro-4,4'-diamino-5,5'-dimethoxybiphenyl, 3,3'-dimethoxy-4,4'-diaminobiphenyl, 4,4'-diamino-2,2'-bis(trifluoromethyl) biphenyl, 2,2'-bis[4-(4-aminophenoxy)phenyl]propane, 2,2-bis[4-(4-aminophenoxy)phenyl]hexafluoropropane, 1,4-bis(4-aminophenoxy)benzene, 4,4'-bis(4-aminophenoxy)-biphenyl, 1,3'-bis(4-aminophenoxy)benzene, 9,9-bis(4-aminophenyl)fluorene, 4,4'-(p-phenyleneisopropylidene) bisaniline, 4,4'-(m-phenyleneisopropylidene)bisaniline, 2,2'-bis[4-(4-amino-2-trifluoromethylphenoxy)phenyl]-hexafluoropropane, 4,4'-bis[4-(4-amino-2-trifluoromethyl) phenoxy]-octafluorobiphenyl; aromatic diamines, such as diaminotetraphenylthiophene, which have two amino groups bonded to an aromatic ring, and a hetero atom other than the nitrogen atoms of the amino groups; aliphatic and alicyclic diamines such as metaxylylene diamine, 1,3-propane diamine, tetramethylenediamine, pentamethylenediamine, octamethylenediamine, nonamethylenediamine, 1,7-diaminoheptamethylenediamine, 1,4-diaminocyclohexane, isophorone diamine, tetrahydrodicyclopentadienylene diamine, hexahydro-4,7-methanoindanilenedimethylene diamine, tricyclo[6,2,1,0$^{2.7}$]-undecylenedimethyl diamine, 4,4'-methylenebis(cyclohexylamine); mono-substituted phenylenediamines represented by the following general formula (13):

(13)

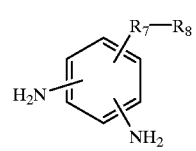

(wherein R7 represents a divalent organic group selected from —O—, —COO—, —OCO—, —CONH— and —CO—, and R8 represents a monovalent organic group having a steroid group); and compounds represented by the following general formula (14):

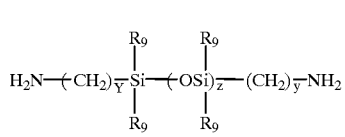

(14)

(wherein R9 represents a hydrocarbon group having 1 to 12 carbons, y is an integer from 1 to 3, and z is an integer from 1 to 20). These diamine compounds may be used either alone or in combination of two or more in addition to 1% of the diamine having the cinnamoyl group.

The polyamic acid obtained as a precursor of the polyimide in the aforesaid manner is thermally or chemically imidized to afford the polyimide composition having the cinnamoyl group. The thermal imidization herein means dehydration imidization which is achieved by adding a tertiary amine and an azeotropic solvent to the aforesaid polyamic acid copolymer. The chemical imidization herein means imidization which is achieved by adding a dehydrating agent and a tertiary amine as a catalyst in amounts not smaller than the stoichiometric amounts to the polyamic acid polymer or a solution thereof, and heating the resulting mixture.

Examples of the dehydrating agent include aliphatic acid anhydrides such as acetic anhydride, and aromatic acid anhydrides. Examples of the catalyst include aliphatic tertiary amines such as triethylamine, aromatic tertiary amines such as dimethylaniline, and heterocyclic tertiary amines such as pyridine, picoline and isoquinoline.

In general, the thermal imidization involves heating at a temperature not lower than 150° C. At a temperature not lower than 180° C., however, the carbon-carbon double bond in the cinnamoyl group or derived cinnamoyl group may undergo a reaction in which the double bond is broken so that the carbons may form bonds with other carbon-carbon double-bond or oxygen. In the present invention, therefore, the thermal imidization with the use of the aforesaid tertiary amine is preferably carried out under temperature conditions of 150° C. to 180° C. to afford the polyimide having the cinnamoyl group. Where the chemical imidization with the use of the acid anhydride is employed in combination with the thermal imidization, the imidization reaction can be carried out at a lower temperature.

The polyamic acid preferably has a weight-average molecular weight of 5,000 to 1,000,000. If the molecular weight is smaller than 5,000, the resulting polyimide composition will have a smaller molecular weight. Therefore, the polyimide composition, if used as it is, is not practical as a photo-reactive resin because of its brittleness. Conversely, if the weight-average molecular weight is greater than 1,000,000, a varnish of the polyamic acid will have an excessively high viscosity, so that the handling thereof is difficult.

Thus, the novel polyimide composition according to the present invention is produced.

Any of various organic additives, inorganic fillers and various reinforcement materials may be added to the polyimide composition.

Next, an explanation will be given to production methods for the respective polyimide compositions, wherein W in the general formula (1) is represented by the formulae (1-b) to (1-e), from diamines each having a cinnamoyl group. The method and conditions for the reduction of the dinitro compound and the method for the production of the polyimide are substantially the same as described above for the polyimide composition of the general formula (1).

A diamine to be used as a starting material for the novel polyimide composition wherein W in the general formula (1) is represented by Ate formula (1-b), more specifically, which comprises a monomer unit represented by the following formula:

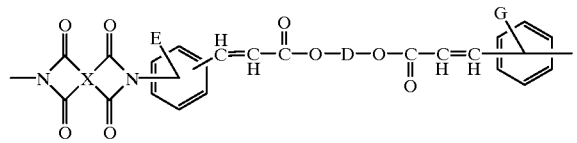

is represented by the general formula (4):

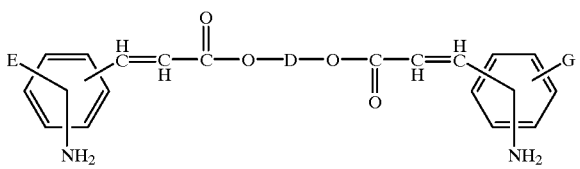

(4)

The diamine can be prepared by reducing a dinitro compound which is prepared by reacting a nitrocinnamic acid derivative or a nitrocinnamoyl chloride derivative with a diol.

More specifically, the nitrocinnamic acid derivative is represented by the formula (2-2):

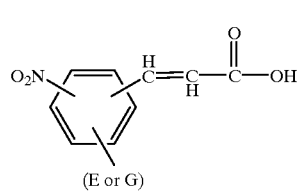

(2-2)

wherein E and G each represent H, $CH_3$, F, Cl, Br or $CH_3O$—.

The nitrocinnamoyl chloride derivative is represented by the formula (2-3):

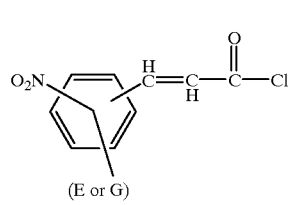

(2-3)

wherein E and G each represent H, $CH_3$, F, Cl, Br or $CH_3O$—.

The diol is a compound having two hydroxyl groups and represented by the formula (2-4):

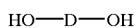
(2-4)

wherein D represents a divalent organic group.

These compounds are reacted with each other to afford a dinitro compound represented by the formula (2-5):

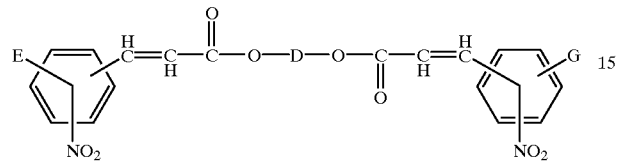
(2-5)

wherein D represents a divalent organic group, and E and G each represent H, $CH_3$, F, Cl, Br or $CH_3O$—. The dinitro compound is reduced to afford the diamine.

In the formulae (2-4) and (2-5), D is a divalent organic group, which is not particularly limited, but examples thereof include the following groups:

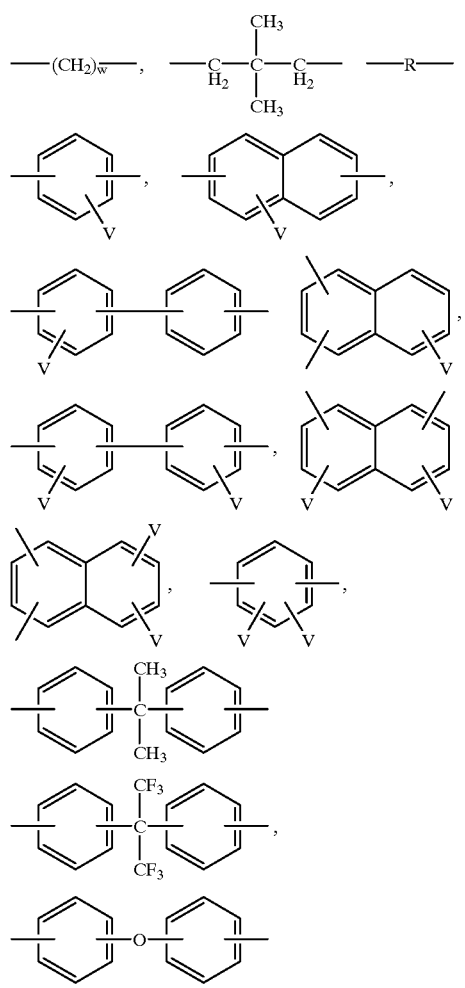

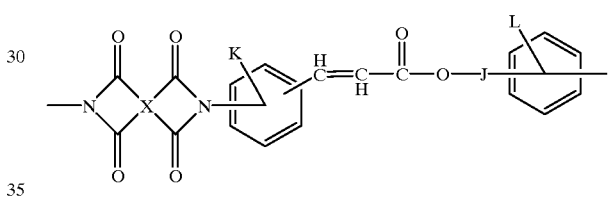

wherein V represents H, $CH_3$, F, Cl, Br or $CH_3O$—.

A diamine to be used as a starting material for the novel polyimide composition wherein W in the general formula (1) is represented by the formula (1-c), more specifically, which comprises a monomer unit represented by the following formula:

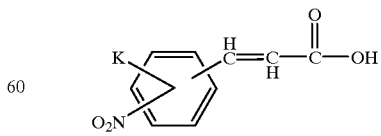

is represented by the general formula (5):

(5)

wherein J represents a divalent organic group, and K and L, which may be the same or different, each represent H, $CH_3$, F, Cl, Br or $CH_3O$—.

For preparation of the diamine, a cinnamic acid derivative represented by the formula (3-2):

(3-2)

(wherein K represents H, $CH_3$, F, Cl, Br or $CH_3O$—) or a cinnamoyl chloride derivative represented by the formula (3-3):

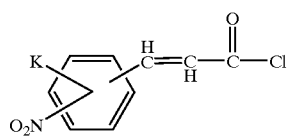
(3-3)

(wherein K represents H, CH$_3$, F, Cl, Br or CH$_3$O—) is reacted with a nitro compound having a hydroxyl group and represented by the formula (3-4):

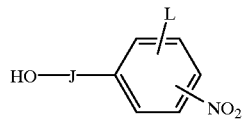
(3-4)

wherein L represents H, CH$_3$, F, Cl, Br or CH$_3$O—, and J represents a divalent organic group) to afford a dinitro compound represented by the formula (3-5):

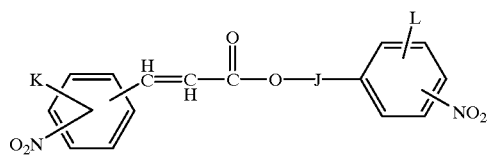
(3-5)

(wherein J represents a divalent organic group, and K and L each represent H, CH$_3$, F, Cl, Br or CH$_3$O—).

The dinitro compound of the formula (3-5) thus prepared is reduced to afford the diamine represented by the general formula (5).

In the formulae (3-4) and (3-5), J is a divalent organic group, which is not particularly limited but may be selected from —CH$_2$—, —(CH$_2$)$_m$— (wherein m=1 to 15), —O—, —(CH$_2$)$_n$— (wherein n=1 to 15) and —OCO—.

A diamine to be used as a starting material for the novel polyimide composition wherein W in the general formula (1) is represented by the formula (1-d), more specifically, which comprises a monomer unit represented by the following formula:

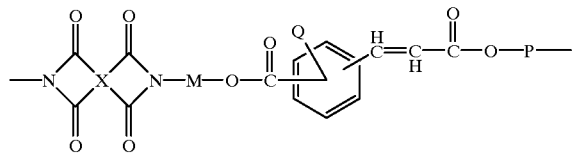

is represented by the general formula (6):

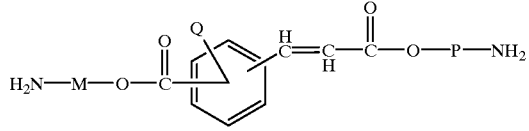
(6)

A cinnamic acid derivative represented by the general formula (4-2):

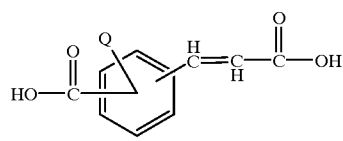
(4-2)

(wherein Q represents H, CH$_3$, F, Cl, Br or CH$_3$O—) or a cinnamoyl chloride derivative represented by the formula (4-3):

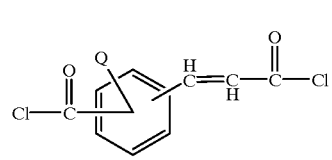
(4-3)

(wherein Q represents H, CH$_3$, F, Cl, Br or CH$_3$O—) is reacted with a nitro compound having a hydroxyl group and represented by the formula (4-4):

$$O_2N—M—OH \text{ or } O_2N—P—OH \qquad (4\text{-}4)$$

(wherein M and P each represent a divalent organic group) to afford a dinitro compound represented by the formula (4-5):

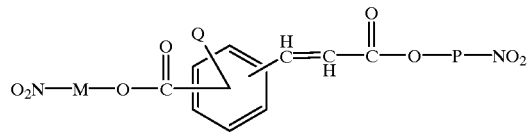
(4-5)

(wherein M and P each represent a divalent organic group, and Q represents H, CH$_3$, F, Cl, Br or CH$_3$O—), and the dinitro compound is reduced to afford the diamine.

In the formulae (4-4) and (4-5), M and P are divalent organic groups which are not particularly limited but may be selected from the following groups:

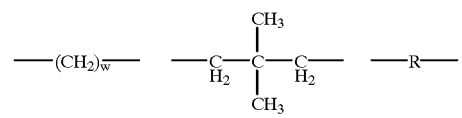
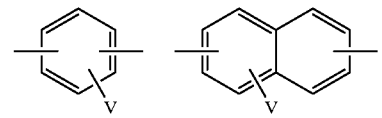
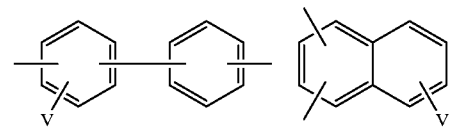

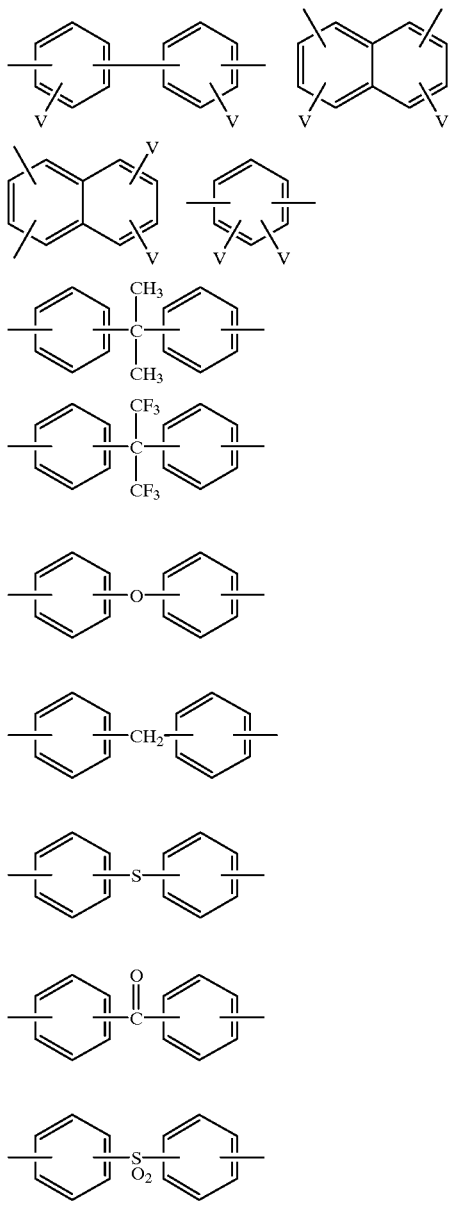

wherein w is an integer from 1 to 40, and V represents H, CH$_3$, F, Cl, Br or CH$_3$O—.

A diamine to be used as a starting material for the novel polyimide composition wherein W in the general formula (1) is represented by the formula (1-e), more specifically, which comprises a monomer unit represented by the following formula:

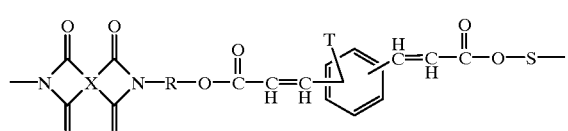

is represented by the general formula (7):

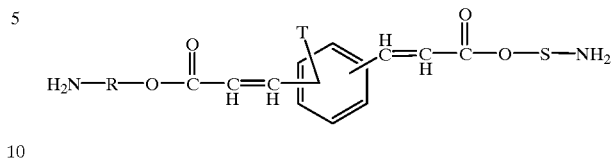

(7)

For preparation of the diamine, a phenylenediacrylic acid derivative represented by the formula (5-2):

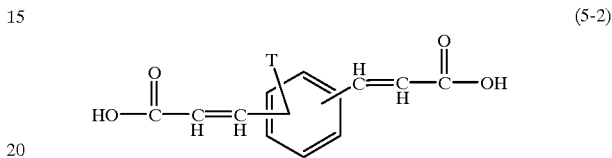

(5-2)

(wherein T represents H, CH$_3$, F, Cl, Br or CH$_3$O—) or a phenylenediacrylic dichloride derivative represented by the formula (5-3):

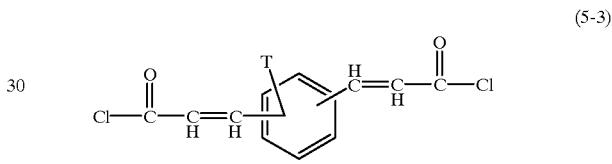

(5-3)

(wherein T represents H, CH$_3$, F, Cl, Br or CH$_3$O—) is reacted with a nitro compound having a hydroxyl group and represented by the formula (5-4):

$$O_2N—R—OH$$

or $$HO—S—NO_2 \quad (5\text{-}4)$$

(wherein R and S each represent a divalent organic group) to afford a dinitro compound represented by the formula (5-5):

(5-5)

(wherein R and S each represent a divalent organic group, and T represents H, CH$_3$, F, Cl, Br or CH$_3$O—).

The dinitro compound thus prepared is reduced to afford the diamine.

In the formulae (5-4) and (5-5), R and S are divalent organic groups, which are not particularly limited but may be selected from the following groups:

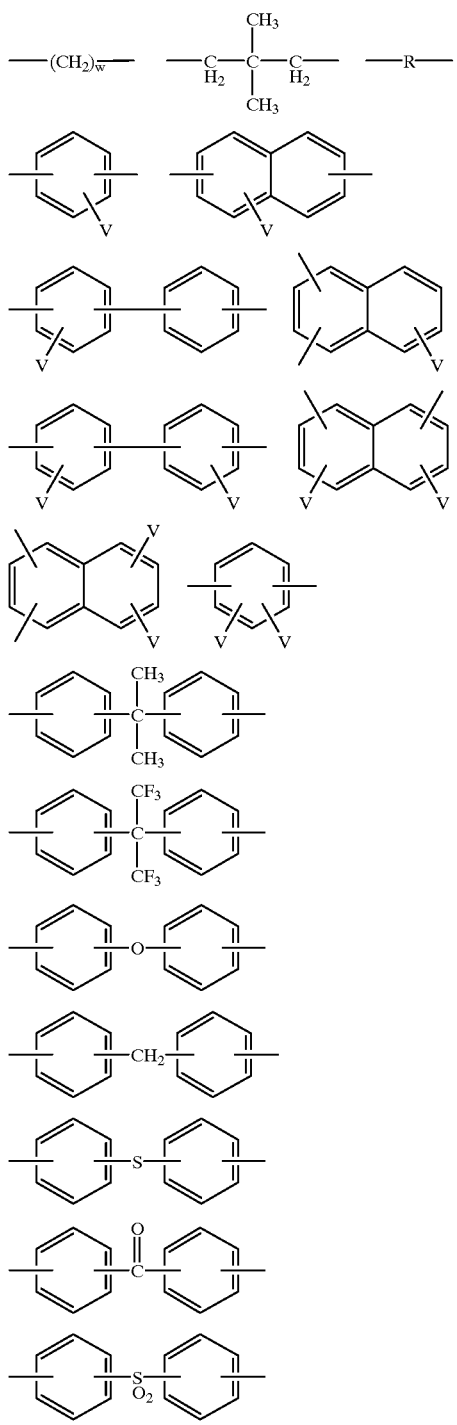

wherein w is an integer from 1 to 40, and V represents H, CH$_3$, F, Cl, Br or CH$_3$O—.

A diamine to be used as a starting material for the novel polyimide composition wherein W in the general formula (1) is represented by the general formula (1-f), more specifically, which comprises a monomer unit represented by the following formula:

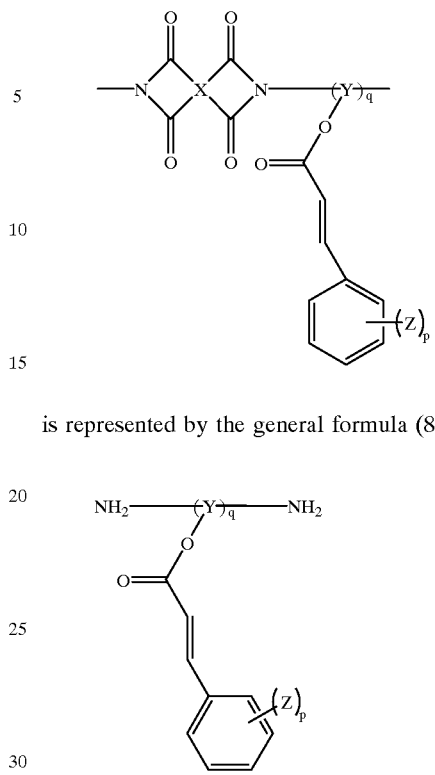

is represented by the general formula (8):

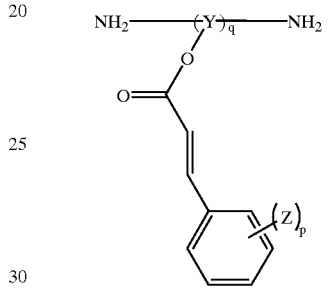

wherein Y represents a trivalent organic group, Z represents H, CH$_3$, F, Cl, Br or CH$_3$O—, p=1 to 3, and q=1 to 3.

The diamine is prepared by reacting a cinnamic acid derivative represented by the formula (6-1):

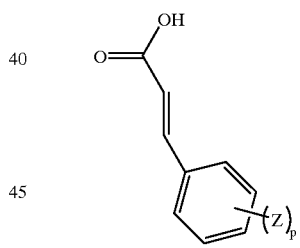

(wherein Z represents H, CH$_3$, F, Cl, Br or CH$_3$O—, and p=1 to 3) or a cinnamoyl chloride derivative represented by the formula (6-2):

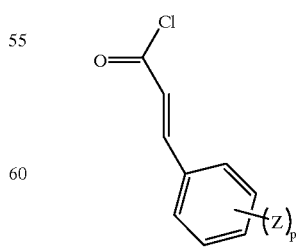

(wherein Z represents H, CH$_3$, F, Cl, Br or CH$_3$O—, and p=1 to 3) with a nitro compound having a hydroxyl group and represented by the formula (6-3):

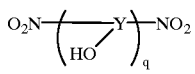
(6-3)

(wherein Y represents a trivalent organic group, and q=1 to 3) to afford a dinitro compound represented by the formula (6-4):

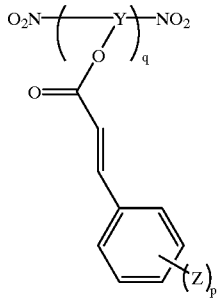
(6-4)

(wherein Y represents a trivalent organic group, Z represents H, CH$_3$, F, Cl, Br or CH$_3$O—, p=1 to 3, and q=1 to 3), and then reducing the dinitro compound. In the formula (6-4), Y is a trivalent organic group, which is not particularly limited but may be selected from the following groups:

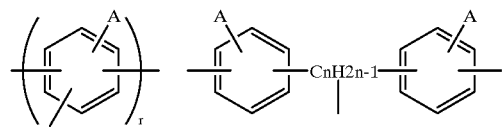

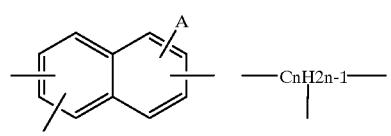

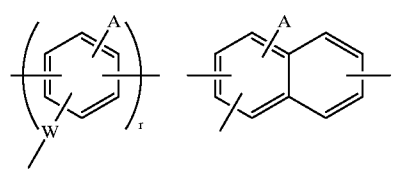

wherein A represents H, CH$_3$, F, Cl, Br or CH$_3$O—, r=1 to 3, n=1 to 20, and W represents a divalent organic group selected from —CH$_2$—, —(CH$_2$)$_m$—O— (wherein m=1 to 15), and —(CH$_2$)$_k$—OCO— (wherein k=1 to 20 (k≠2)).

The dinitro compound is hydrogenated under the aforesaid reduction conditions to afford the diamine represented by the general formula (8):

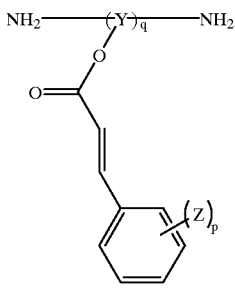
(8)

wherein Y represents a trivalent organic group, Z represents H, CH$_3$, F, Cl, Br or CH$_3$O—, p=1 to 3, and q=1 to 3.

Next, an explanation will be given to the polyimide composition production method (2) in which a diol-terminated polyimide oligomer is reacted with a dicarboxylic acid or dicarboxylic acid chloride having a cinnamoyl group to form ester linkage for polymerization, thereby affording the polyimide composition.

The polyimide composition wherein W in the general formula (1) is represented by the formula (1-a) is obtained by reacting a dicarboxylic acid represented by the following formula:

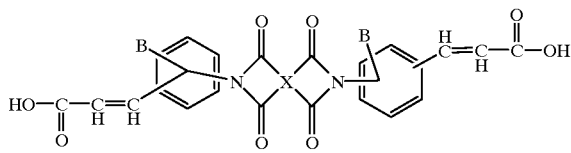

or an acid chloride thereof with a diol represented by the following formula:

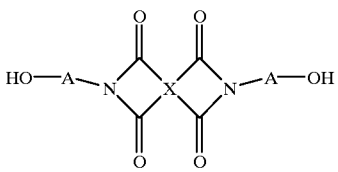

for formation of ester linkage.

The polyimide composition wherein W in the general formula (1) is represented by the formula (1-b) is obtained by reacting a dicarboxylic acid represented by the following formula:

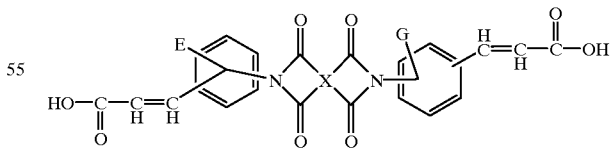

or an acid chloride thereof with a diol represented by the following formula:

HO—D—OH for formation of ester linkage.

The polyimide composition wherein W in the general formula (1) is represented by the formula (1-c) is obtained by reacting a dicarboxylic acid represented by the following formula:

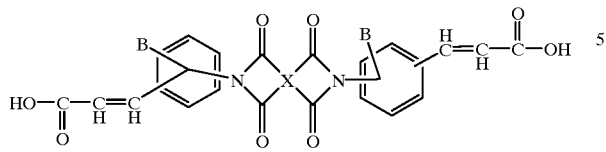

(wherein B represents H, CH$_3$, F, Cl, Br or CH$_3$O—) or an acid chloride thereof with a diol represented by the following formula:

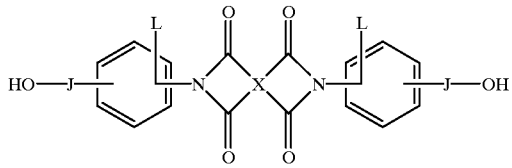

(wherein L represents H, CH$_3$, F, Cl, Br or CH$_3$O—) for formation of ester linkage.

The polyimide composition wherein W in the general formula (1) is represented by the formula (1-d) is obtained by reacting a dicarboxylic acid represented by the following formula:

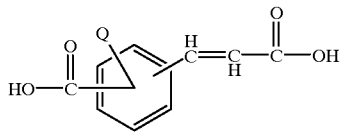

or an acid chloride thereof with a diol represented by the following formula:

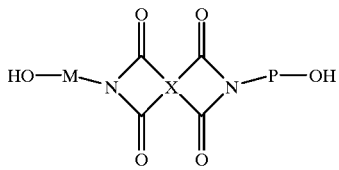

for formation of ester linkage.

The polyimide composition wherein W in the general formula (1) is represented by the formula (1-e) is obtained by reacting a dicarboxylic acid represented by the following formula:

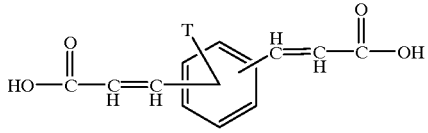

or an acid chloride thereof with a diol represented by the following formula:

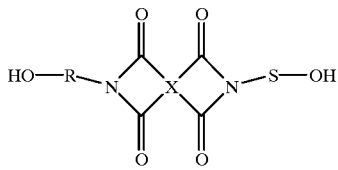

for formation of ester linkage.

In the polyimide composition synthesizing methods, in which these diol-terminated polyimide oligomers are each reacted with the corresponding dicarboxylic acid or diacid chloride having the cinnamoyl group to form ester linkage for production of the polyimide composition, the resulting polymer tends to have a higher molecular weight where the diol is attributed to alcoholic hydroxyl groups than where the diol is attributed to phenolic hydroxyl groups.

An exemplary production method for a polyimide having a cinnamoyl group incorporated in an acid dianhydride residue thereof is such that an acid dianhydride having the cinnamoyl group is first reacted with a diamine.

Preparation methods for novel acid dianhydrides will hereinafter be described more specifically.

An explanation will first be given to preparation methods for novel acid dianhydrides having a cinnamoyl group and, for example, represented by the general formula (9):

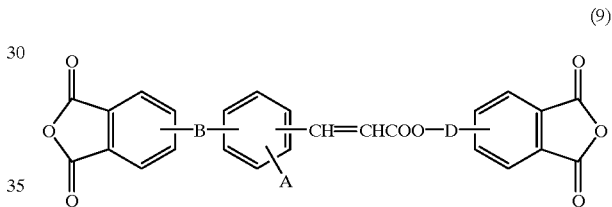

(9)

For formation of —COO— linkage as B in the general formula (9), synthesis is carried out by reacting anhydrous trimellitic chloride with HO—C$_6$H$_4$(A)CH=CHCOO— (wherein A represents H, CH$_3$, F, Cl, Br or CH$_3$O—, which is hereinafter the same).

For formation of —OCO— linkage as B in the general formula (9), synthesis is carried out by reacting hydroxyphthalic anhydride with ClCO—C$_6$H$_4$(A)CH=CHCOO—.

For formation of —O— linkage as B in the general formula (9), synthesis is carried out by reacting chlorophthalic anhydride with HO—C$_6$H$_4$(A)CH=CHCOO—.

For formation of —OEO— linkage as B in the general formula (9), synthesis is carried out by reacting monohalogenated phthalic anhydride with a halogenated compound such as having Cl—C$_6$H$_4$(A)CH=CHCOO— and a diol represented by HO—E—OH (wherein E represents a benzene ring, a naphthalene ring, a biphenyl or —C$_m$H$_{2m}$— (wherein m represents an integer from 1 to 20), which is hereinafter the same).

For formation of —COOEOCO— linkage as B in the general formula (9), synthesis is carried out by reacting anhydrous trimellitic chloride with ClCO—C$_6$H$_4$(A) CH=CHCOO— and a diol represented by HO—E—OH.

For formation of —OOCCH=CH— linkage as B in the general formula (9), synthesis is carried out by reacting phenylene acrylic acid or phenylene acrylic chloride with hydroxyphthalic anhydride.

Similarly, for formation of —O—EOCO— or —O—E—COO— linkage as B in the general formula (9), synthesis is carried out by reacting a halogenated compound with HO— for ether linkage or by reacting a carboxylic acid or an acid chloride with HO— for ester linkage.

For formation of single bond as D in the general formula (9), synthesis is carried out by reacting hydroxyphthalic anhydride with ClCO—CH=CHC$_6$H$_4$(A)—.

For formation of —F—OCO— linkage as D in the general formula (9), synthesis is carried out by linking anhydrous trimellitic chloride to —C$_6$H$_4$(A) CH=CHCOCl— with a diol represented by HO—F—OH (wherein F represents a benzene ring, a naphthalene ring, a biphenyl or —C$_m$H$_{2m}$— wherein m represents an integer from 1 to 20).

For formation of —F—O— linkage as D in the general formula (9), synthesis is carried out by reacting ClCO—CH=CH—C$_6$H$_4$(A)— with HO—F—Cl to afford Cl—F—OCO—CH=CHC$_6$H$_4$(A)— which is in turn reacted with hydroxyphthalic anhydride.

An explanation will next be given to preparation methods for novel acid dianhydrides having a cinnamoyl group or a derived cinnamoyl group incorporated in a side chain thereof and represented by the general formula (10):

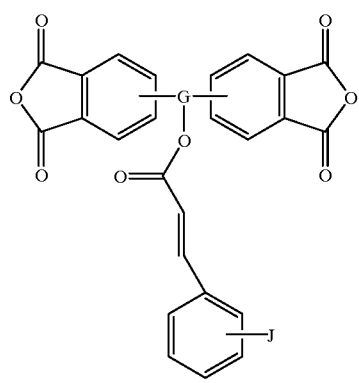

(10)

For example, Cl—K(OH)—Cl is reacted with cinnamoyl chloride or an acid chloride of a cinnamic acid derivative having H, CH$_3$, F, Cl, Br, CH$_3$O— or the like introduced onto a benzene ring of cinnamoyl chloride to afford a dichloride of the formula (10-1):

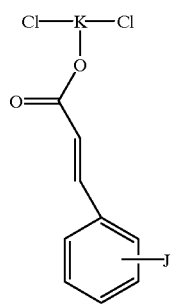

(10-1)

wherein J represents H, CH$_3$, F, Cl, Br, CH$_3$O— or the like.

The dichloride of the general formula (10-1) is reacted with hydroxyphthalic anhydride to afford an acid dianhydride represented by the formula (10-A):

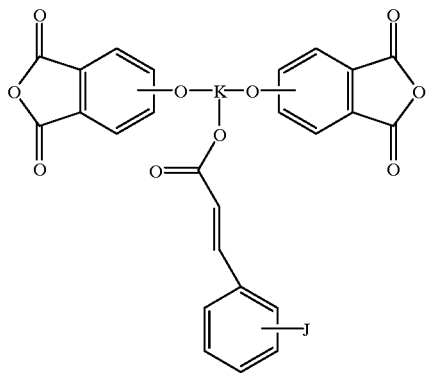

(10-A)

wherein J represents H, CH$_3$, F, Cl, Br, CH$_3$O— or the like.

The acid dianhydride represented by the formula (10-A) can also be obtained by the following method.

A triol represented by HO—K(OH)—OH is reacted with cinnamoyl chloride or an acid chloride of a cinnamic acid derivative having H, CH$_3$, F, Cl, Br, CH$_3$O— or the like introduced onto a benzene ring of cinnamoyl chloride to afford a diol of the formula (10-2):

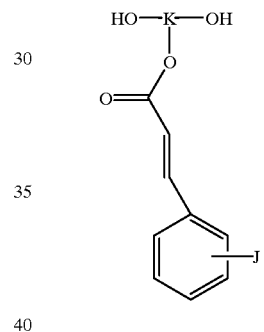

(10-2)

wherein J represents H, CH$_3$, F, Cl, Br, CH$_3$O— or the like.

The diol is reacted with monohalogenated phthalic anhydride to afford the novel acid dianhydride represented by the formula (10-A).

Further, a novel acid dianhydride represented by the formula (10-B):

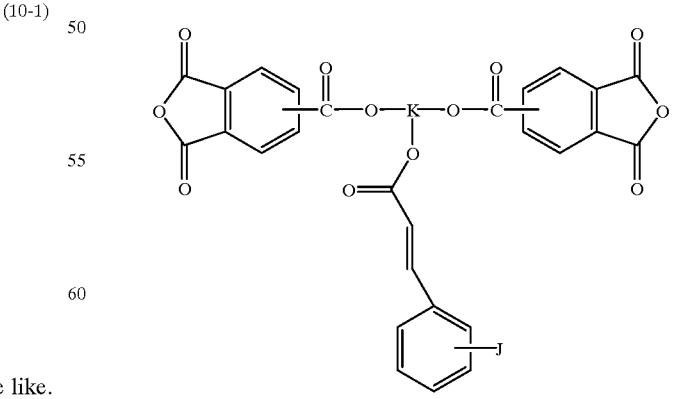

(10-B)

is obtained by reacting anhydrous trimellitic chloride with the diol of the formula (10-2).

Further, CH$_3$OCO—K(OH)COOCH$_3$ is reacted with cinnamoyl chloride or an acid chloride of a cinnamic acid derivative having H, CH$_3$, F, Cl, Br, CH$_3$O— or the like introduced onto a benzene ring of cinnamoyl chloride to afford a compound represented by the formula (10-3):

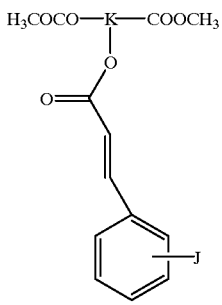

(10-3)

This compound is reacted with hydroxyphthalic anhydride for ester interchange to afford a novel acid dianhydride represented by the formula (10—C):

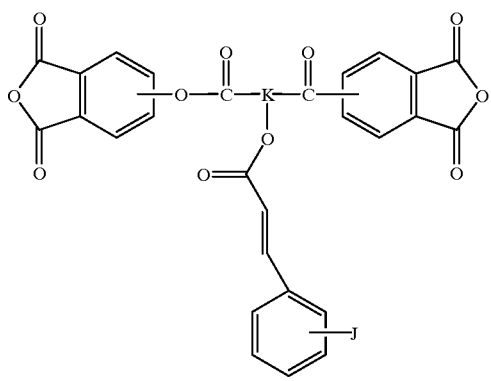

(10-C)

The novel acid dianhydride of the general formula (9) obtained through the aforesaid reaction has the cinnamoyl group or derived cinnamoyl group incorporated in a main chain thereof, while the novel acid dianhydride of the general formula (10) has the cinnamoyl group or derived cinnamoyl group incorporated in a side chain thereof. These acid dianhydrides are useful as monomers for the novel polyimide compositions having photo-reactivity and heat-reactivity which are inherent in cinnamoyl group.

There will next be described methods for synthesizing the polyimide compositions.

In addition to the acid dianhydride represented by the general formula (9) or (10), other acid dianhydrides may be used for the polyamide compositions having a cinnamoyl group or a derived cinnamoyl group according to the present invention. If the acid dianhydride represented by the general formula (9) or (10) is contained in a proportion of not smaller than 1% based on the total amount of the acid dianhydrides, the polyimide composition according to the present invention can exhibit properties inherent in the cinnamoyl group.

The novel acid dianhydride having the cinnamoyl group or derived cinnamoyl group incorporated in its main chain or side chain as represented by the general formula (9) or (10) is reacted with a diamine in an organic polar solvent to afford a polyamic acid, which is thermally and chemically imidized to afford the polyimide composition having the cinnamoyl group. The polyimide production method is the same as described above. The diamine having no cinnamoyl group and the other acid dianhydride to be herein used are the same as described above.

As described above, the novel polyimide compositions according to the present invention can be produced with the use of the diamine or the acid dianhydride having the cinnamoyl group. Other production methods for the polyimide compositions having the cinnamoyl group according to the invention will be described below.

An acid dianhydride having a hydroxyl group is reacted with a given diamine to afford an amic acid, which is then dehydrated for ring closure to afford a hydroxyl-terminated imide oligomer. The imide is reacted with a dicarboxylic acid derived from cinnamic acid or an acid chloride thereof for formation of ester linkage, thereby affording a polyimide composition having a cinnamoyl group or a derived cinnamoyl group in a main chain thereof, wherein X in the general formula (2) is, for example, represented by the formula (2-a), more specifically, which comprises a monomer unit represented by the following formula:

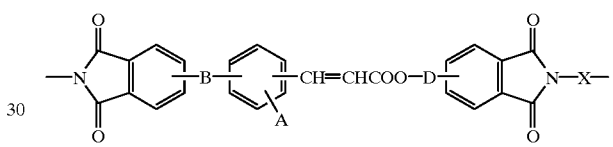

Further, where the hydroxyl-terminated imide oligomer is reacted with a compound represented by any of the following formulae:

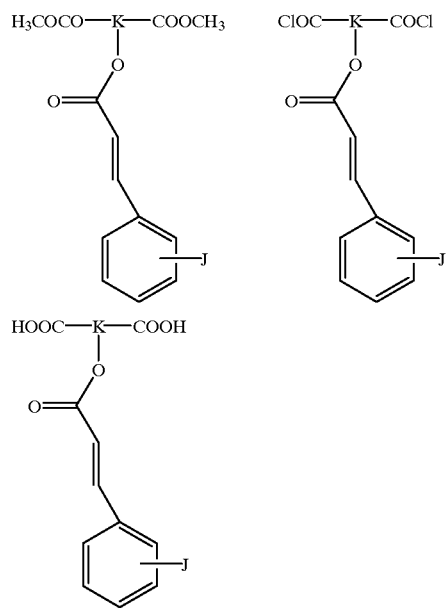

a polyimide composition having a cinnamoyl group or a derived cinnamoyl group, wherein X in the general formula (2) is represented by the formula (2-2), more specifically, which comprises a monomer unit represented by the following formula:

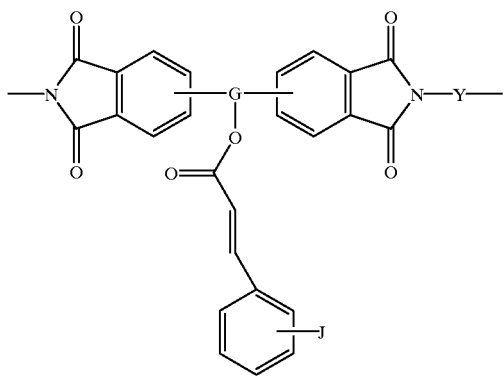

can be obtained.

In another polyimide composition production method according to the present invention, trimellitic anhydride is reacted with a given diamine to afford an amic acid, which is then dehydrated for ring closure to afford a carboxyl-terminated imide oligomer. The imide is reacted with a diol derived from cinnamic acid for formation of ester linkage, thereby affording a polyimide composition having a cinnamoyl group.

More specifically, the carboxyl-terminated imide oligomer is reacted with a compound represented by either of the following formulae:

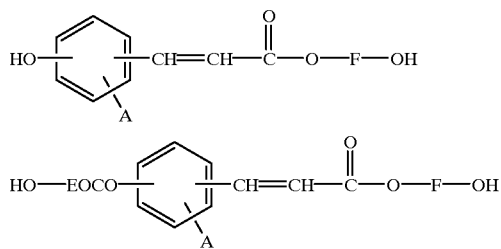

(wherein E represents a benzene ring, a naphthalene ring, biphenyl or —$C_mH_{2m}$— (wherein m represents an integer from 1 to 20), and F represents —$C_mH_{2m}$— (wherein m represents an integer from 1 to 20), a benzene ring or a naphthalene ring to afford the polyimide composition having a monomer unit represented by the general formula (1) and having a cinnamoyl group or a derived cinnamoyl group incorporated in a main chain.

Further, where the carboxyl-terminated imide oligomer is reacted with a diol represented by the formula (10-2):

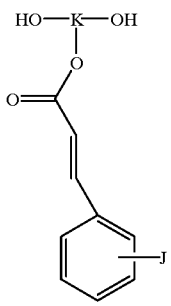

(10-2)

the polyimide composition having the monomer unit represented by the general formula (2) and having a cinnamoyl group or a derived cinnamoyl group can be obtained.

Any of various organic additives, inorganic fillers and various reinforcement agents may be added to the polyimide compositions thus obtained in accordance with the present invention.

The novel polyimide compositions of the present invention produced in the aforesaid manner have the cinnamoyl group and, therefore, exhibit heat-or photo-reactive and cross-linkable properties inherent in the cinnamoyl group in addition to various excellent properties inherent in the conventional polyimides. Therefore, the novel polyimide compositions of the invention will find new applications as excellent thermosetting resins and heat-reactive resins which are reactive at particular temperatures and/or at particular wavelengths.

EXAMPLES

The present invention will hereinafter be described more particularly by showing examples thereof, which examples, however, are merely intended to be illustrative and not to be construed as limiting the scope of the invention.

Out of examples, ESDA expresses 2,2-bis(4-hydroxyphenyl)propanedibenzoate-3,3',4,4'-tetracarboxylic acid dianhydride, 6FDA expresses 2,2'-hexafluoropropylidenediphthalic acid dianhydride, DMAc expresses N,N-dimethylacetamide, and DMF expresses N,N-Dimethylformamide.

An "Exothermic peak temperature" is a peak temperature when measuring a temperature range from room temperature to 400° C. at the rate of rise in temperature of 10° C./minute under a nitrogen atmosphere using a DSC CELL SCC-41 (differential scanning calorimeter produced by Shimadz Corporation). The exothermic peak temperature is approximately 230° C. when dimerizing carbon-carbon double bond.

The "weight-average molecular weight" is measured by using a GPC (produced by Waters Corporation) under the following conditions:

Column: 2 pieces of KD-806M (produced by Shodex)
Temperature: 60° C.
Detector: RI (Refractive Index)
Flow rate: 1 ml/minute
Developer: DMF (lithium bromide 0.03M, phosphoric acid 0.03M)
Concentration of sample solution: 0.2wt %
Injection amount: 20 µl
Reference material: polyethylene oxide In the following examples 1 through 9, a novel diamine having a cinnamic acid skeleton was produced to synthesize a polyimide composition.

Example 1

(1) Synthesis of 3,5-dinitrobenzil-cinnamate 59.44 g (0.3 mole) of 3,5dinitrobenzil alcohol, 66.64 g (0.4 mole) of cinnamoyl chloride, and 700 ml of o-dichlorobenzene were placed in a reaction vessel and they were heated in the range of 120° C. to 130° C. for 2 hours under a nitrogen current with stirring. After the completion of the reaction, the reacted solution was poured into hexane to obtain a precipitate. A precipitate was purified by recrystallization, and 85 g of 3,5-dinitrobenzil cinnamate was yielded.

(2) Synthesis of 3,5-diaminobenzil cinnamate 65.6 g (200 milimole) of 3,5-dinitrobenzil cinnamate, 10 g carbon black contained 5% Pt (product with water content of about 50%), and 500 ml of 1,4-dioxane were placed in a reaction vessel (hydrogenating apparatus). Then the reaction mixture were heated at 60° C. with stirring under a hydrogen atmosphere. In approximately two hours, 29 L of hydrogen was absorbed and the reaction was completed when the absorption of hydrogen stopped, and the filtrate was concentrated. The carbon black contained Pt was isolated by filtration. Thus, 53.6 g of 3,5 -diaminobenzil cinnamate was yielded. The exothermic peak temperature was 230° C.

(3) Synthesis of polyimide 26.8 g (0.1 mole) of 3,5-diaminobenzil cinnamate and 300 g of DMAc were placed in a 2,000 ml-separable flask equipped with a stirrer. 57.65 g (0.1 mole) of ESDA was added while vigorously stirring and the stirring was continued for 30 minutes. For imidization, 9.3 g (0.20 mole) of β-picoline, 50 g of acetic anhydride, and 100 g of DMAc were added to the above reacted solution, and then heated at approximately 150° C. Such reaction was performed under a nitrogen current. After the completion of the reaction, the reacted solution was poured into methanol. The reactant was filtered and dried. Thus, 73 g of polyimide was yielded as yellow powder. The weight-average molecular weight of this polyimide powder was 80,000.

Example 2

(1) Synthesis of 2,4-dinitrophenyl cinnamate 66.64 g (0.4 mole) of cinnamoyl chloride and 300 g of methyl ketone (hereinafter referred to as MEK) were placed in a reaction vessel to be stirred by heating at 60° C. under a nitrogen current. 73.64 g (0.4 mole) of 2,4-dinitrophenol, 50 g of pyridine, and 500 g of MEK were added dropwise to the above reaction vessel using a dropping funnel. After that, reflux stirring was conducted for approximately 20 hours under a nitrogen current. After the completion of the reaction, the precipitate was separated by filtration. The filtrate was concentrated until crystals separated out and poured into methanol. 90 g of light yellow colored needle-like crystals (2,4-dinitrophenyl cinnamate) were yielded.

(2) Synthesis of 2,4-diaminophenyl cinnamate 62.8 g (200 milimole) of 2,4-dinitrophenyl cinnamate, 15 g of carbon black with 5% Pt and 2% iron (product with water content of about 50%), and 500 ml of 1,4-dioxane were placed in a reaction vessel (hydrogenating apparatus), and then the reaction mixtures were heated at 60° C. with stirring under a hydrogen atmosphere. In approximately 20 hours, 14.50 L of hydrogen was absorbed, and the reaction was completed when the absorption of hydrogen stopped. Then the reacted solution was separated by filtration to remove the catalyst. The filtrate was concentrated, and 50.8 g of 2,4-diaminophenyl cinnamate was yielded. The exothermic peak temperature was 230° C.

(3) Synthesis of polyimide 25.4 g (0.1 mole) of 2,4-diaminophenyl cinnamate and 300 g of DMAc were placed in a 2,000 ml-separable flask equipped with a stirrer. 57.65 g (0.1 mole) of ESDA was added while vigorously stirring and the stirring was continued for 30 minutes. For imidization, 9.3 g (0.2 mole) of β-picoline, 50 g of acetic anhydride, and 100 g of DMAc were added to the above reacted solution, and then heated at approximately 150° C. Such reaction was performed under a nitrogen current. After the completion of the reaction, the reacted solution was poured into methanol, and the reactant was filtered and dried. 79 g of polyimide was yielded as yellow powder. The weight-average molecular weight of the polyimide powder was 100,000.

Example 3

(1) Synthesis of 2-(2,4-dinitrophenoxy)ethyl-1-cinnamate 20.25 g (0.1 mole) of 2,4-dinitrochlorobenzene, 124 g (2 moles) of ethylene glycol, 82.93 g (0.6 mole) of potassium carbonate, and 600 ml of xylene were placed in a reaction vessel to be stirred by heating for 12 hours. The reacted solution was isolated by filtration, and the filtrate was concentrated. 17.0 g of 2-(2,4-dinitrophenoxy) ethanol was yielded by column purification.

10.65 g (0.05 mole) of 2-(2,4-dinitrophenoxy) ethanol, 8.33 g (0.05 mole) of cinnamoyl chloride, and 100 ml of o-dichlorobenzene were stirred in the range of 120 to 130° C. under a nitrogen current for 2 hours. After the completion of the reaction, a precipitate was obtained by pouring the reacted solution into hexane. The precipitate was purified by recrystallization. 15.4 g of 2-(2,4-dinitrophenoxy)ethyl-1-cinnamate was yielded.

(2) Synthesis of 2-(2,4-diaminophenoxy)ethyl-1-cinnamate 2-(2,4-diaminophenoxy)ethyl-1-cinnamate was obtained by reduction made in the same manner as in Example 2. The exothermic peak temperature was 232° C.

(3) Synthesis of polyimide 14.4 g (0.1 mole) of 2-(2,4-diaminophenoxy)ethyl-1-cinnamate and 150 g of DMAc were placed in a 1,000 ml-separable flask equipped with a stirrer. 22.2 g (0.1 mole) of 6FDA was added while vigorously stirring and the stirring was continued for 30 minutes. For imidization, 9.3 g of (0.2 mole) β-picoline, 50 g of acetic anhydride, and 100 g of DMAc were added to the above reacted solution, and then the reacted solution was heated at approximately 150° C. Such reaction was performed under a nitrogen current. After the completion of the reaction, the reacted solution was poured into methanol, and the reactant was separated by filtration and dried. 34 g of polyimide was yielded as white powder. The weight-average molecular weight of the polyimide powder was 110,000.

Example 4

(1) Synthesis of 2-(3,5-dinitrobenzoic acid)propyl-1-cinnamate

Excess propylene glycol (approximately 10 times as many moles as cinnamic chloride) was placed in a container to be cooled by ice. Cinnamic chloride was added to this, and the reaction mixtures were heated in the range of 120 to 130° C. with stirring under a nitrogen current for approximately 2 hours. The reaction mixture solution was extracted with dichloromethane to be concentrated. Such concentrate was purified by a column chromatography. 2-(2,4-dinitrobenzoic acid)propyl-1-cinnamate was obtained in a 70% yield.

(2) Synthesis of 3,5-dinitrobenzoic acid chloride 3,5 dinitrobenzoic acid and ethyl acetate were placed in a reaction vessel. While thionyl chloride with some drops of DMF (about double as many moles as dinitrobenzoic acid) was dropped into the reaction mixtures, the reaction mixtures were refluxed with stirring until the generation of hydrogen chloride gas stopped. The reacted solution was concentrated until a solid could be precipitated and was poured into hexane and then the precipitated solid was separated by filtration. 3,5-dinitrobenzoic chloride was obtained in a 90% yield.

(3) Synthesis of 2-(3,5-diaminobenzoic acid)propyl-1cinnamate 2-(3,5-diaminobenzoic acid)ethyl-1-cinnamate was obtained by reduction made in the same manner as in Example 2. The exothermic peak temperature was 233° C.

(4) Synthesis of polyimide 34.0 g (0.1 mole) of 2-(3,5-diaminobenzoic acid)propyl-1-cinnamate and 300 g of DMAc were placed in a 2,000 ml-separable flask equipped with a stirrer. 44.4 g (0.1 mole) of 6FDA was added while vigorously stirring and the stirring was continued for 30 minutes. For imidization, 9.3 g (0.2 mole) of β-picoline, 50 g of acetic anhydride, and 100 g of DMAc were added to the above reacted solution, and then heated at approximately 150° C. Such reaction was performed under a nitrogen current. After the completion of the reaction, the reacted solution was poured into methanol, and separated by filtration and the filtrate was dried. 74.5 g of polyimide was yielded as white powder. The weight-average molecular weight of the polyimide powder was 100,000.

Example 5

(1) Synthesis of (4'-nitrophenyl)-4-nitrocinnamate 193.2 g (1 mole) of 4-nitrocinnamic acid and 650 g of ethyl acetate were placed in a reaction vessel. While 200 g of thionyl chloride with some drops of DMF was dropped into the reaction mixtures, the reaction mixtures were refluxed with stirring until the generation of hydrogen chloride gas stopped. The reacted solution was concentrated until a solid could be precipitated and was poured into hexane and then the precipitated solid was separated by filtration and dried. 210 g of 4-nitrocinnamoyl chloride was yielded. 64.5 g (0.3 mole) of 4-nitrocinnamoyl chloride and 300 g of acetone were placed in a reaction vessel. The reaction mixtures were heated at 50° C. with stirring under a nitrogen current. 41.73 g (0.3 mole) of 4-nitrophenol, 60 g of pyridine, and 300 g of acetone were added dropwise to the above reaction vessel using a dropping funnel. After the completion of the addition, the reaction mixtures were refluxed with stirring under a nitrogen current for 2 hours. After the reaction, a precipitate was separated by filtration, and the filtrated solid was washed by water and dried. 90 g of light yellow colored needle-like crystals ((4-nitrophenyl)-4-cinnamate)was yielded.

(2) Synthesis of (4-aminophenyl)-4-aminocinnamate 6.91 g (22 milimole) of (4-nitrophenyl)-4-cinnamate), 0.6 g of carbon black containing 5% Pt and 2% sodium (product with water content of about 50%), and 100 ml of 1,4-dioxane were placed in a reaction vessel (hydrogenating apparatus), and then the reaction mixtures were heated at 60° C. with stirring under a hydrogen atmosphere. 3.17 L of hydrogen was absorbed in approximately 4 hours, and the reaction was completed because the absorption of hydrogen stopped. And the reacted solution was filtered for removing carbon containing Pt. The filtrate was concentrated and recrystallized. 4.9 g of (4'-aminophenyl)-4-aminocinnamate was yielded. The exothermic peak temperature was 233° C.

(3) Synthesis of polyimide 25.4 g (0.1 mole) of (4'-aminophenyl)-4-aminocinnamate and 300 g of DMAc were placed in a 2,000 ml-separable flask equipped with a stirrer. 44.4 g (0.1 mole) of 6FDA was added while vigorously stirring and the stirring was continued for 30 minutes. For imidization, 9.3 g (0.2 mole) of β-picoline, 50 g of acetic anhydride, and 100 g of DMAc were added to the above reaction solution, and the reaction solution was heated at approximately 150° C. Such reaction was performed under a nitrogen current. After the completion of the reaction, the reacted solution was poured into methanol, and the precipitate was separated by filtration and dried. 66 g of polyimide was yielded as white powder. The weight-average molecular weight of the polyimide powder was 120,000.

Example 6

(1) Synthesis of (3'-nitrophenyl)-3-nitrocinnamate 193.2 g (1 mole) of 3-nitrocinnamic acid and 650 g of ethyl acetate were placed in a reaction vessel. While 200 g of thionyl chloride with some drops of DMF was dropped into the reaction mixtures, the reaction mixtures were refluxed with stirring until the generation of hydrogen chloride gas stopped. The reacted solution was concentrated until a solid could be precipitated and poured into hexane. The precipitate was separated by filtration and dried. 205 g of 3-nitrocinnamoyl chloride was yielded.

64.5 g (0.3 mole) of 3-nitrocinnamoyl chloride and 300 g of acetone were placed in a reaction vessel and stirred at 50° C. under a nitrogen current. 41.73 g (0.3 mole) of 3-nitrophenol, 60 g of pyridine, and 300 g of acetone were added dropwise to the above reaction vessel using a dropping funnel. After the completion of the addition, the reaction mixtures were stirred under a nitrogen current for 2 hours. After the reaction, the solid obtained by concentrating the solution was washed by water and dried. 85 g of light yellow colored needle-like crystals ((3-nitrophenyl)-3-cinnamate) was yielded.

(2) Synthesis of (3-aminophenyl)-3-aminocinnamate 6.91 g (22 milimole) of (3-nitrophenyl)-3-cinnamate), 0.5 g of carbon black containing 5% Pt (product with water content of about 50%), and 100 ml of 1,4-dioxane were placed in a reaction vessel (hydrogenating apparatus), and the reaction mixture was stirred at 60° C. under a hydrogen atmosphere. 3.15 L of hydrogen was absorbed in approximately 4 hours, and the reaction was completed when the absorption of hydrogen stopped. Then the reacted solution was filtered for removing carbon containing Pt. The filtrate was concentrated and recrystallized. 4.0 g of (3'-aminophenyl)-3-aminocinnamate was yielded. The exothermic peak temperature was 233° C.

(3) Synthesis of polyimide 25.4 g (0.1 mole) of (3'-aminophenyl)-3-aminocinnamate and 300 g of DMAc were placed in a 2,000 ml-separable flask equipped with a stirrer. 44.4 g (0.1 mole) of 6FDA was added while vigorously stirring and the reaction mixture was stirred for 30 minutes. For imidization, 9.3 g (0.2 mole) of β-picoline, 50 g of acetic anhydride, and 100 g of DMAc were added to the above reaction solution, and then heated at approximately 150° C. Such reaction was performed under a nitrogen current. After the completion of the reaction, the reacted solution was poured into methanol, and separated by filtration and dried. 65 g of polyimide was yielded as white powder. The weight-average molecular weight of the polyimide powder was 100,000.

Example 7

(1) Synthesis of 1'-nitro-2'-naphthyl-(3-nitrocinnamate)

21.5 g (0.1 mole) of 3-nitrocinnamoyl chloride in Example 2 and 300 g of acetone obtained were placed in a reaction vessel and the reaction mixture was stirred at 50° C. under a nitrogen current. 18.9 g (0.1 mole) of 1-nitro-2-naphthol, 20 g of pyridine, and 300 g of acetone were added dropwise to the above reaction vessel using a dropping funnel. After the completion of the addition, the reaction mixture was refluxed with stirring under a nitrogen current for 2 hours. After the reaction, the solid obtained by concentrating the solution was washed by water and dried. 35 g of light yellow colored needle-like crystals ((1-nitro-2'-naphthol)-3-nitrocinnamate) was yielded.

(2) Synthesis of 1'-amino-2'-naphthyl-(3-aminocinnamate)

7.28 g (20 milimole) of 1'-nitro -2'-naphthyl-(3-nitrocinnamate), 0.5 g of carbon black containing 5% Pt (product with water content of approximately 50%), and 100 ml of 1,4-dioxane were placed in a reaction vessel (hydrogenating apparatus), and then the reaction solution was stirred at 60° C. under a hydrogen atmosphere. 2.9 L of hydrogen was absorbed in approximately 4 hours, and the reaction was completed when the absorption of hydrogen stopped. Then the reacted solution was filtered for removing carbon containing Pt and the filtrate was condensed and recrystallized. 4.5 g of 1'-amino-2'-naphythyl-(3-aminocinnamate)was yielded. The exothermic peak temperature was 231° C.

(3) Synthesis of polyimide 30.4 g (0.1 mole) of 1'-amino-2'-naphthyl-(3-aminocinnamate) and 300 g of DMAc were placed in a 2,000 ml-separable flask equipped with a stirrer. 44.4 g (0.1 mole) of 6FDA was added while vigorously stirring and stirred for 30 minutes. For imidization, 9.3 g (0.2 mole) of β-picoline, 50 g of acetic anhydride, and 100 g of DMAc were added to the above reaction solution, and then heated at approximately 150° C. Such reaction was performed under a nitrogen current. After the completion of the reaction, the reacted solution was poured into methanol, and the precipitate was separated by filtration and dried. 70 g of polyimide was yielded as white powder. The weight-average molecular weight of the polyimide powder was 130,000.

Example 8

(1) Synthesis of 1,3-bis (4-nitro cinnamic acid) benzene 193.2 g (1 mole) of 4-nitrocinnamic acid and 650 g of ethyl acetate were placed in a reaction vessel. While 200 g of thionyl chloride with some drops of DMF was dropped into the reaction mixture, the reaction mixture was refluxed with stirring until the generation of hydrogen chloride gas stopped. The reacted solution was concentrated until a solid could be precipitated and then poured into hexane. The precipitated solid was separated by filtration and dried. 210 g of 4-nitrocinnamoyl chloride was yielded. 63.5 g (0.3 mole) of 4nitrocinnamoyl chloride and 400 g of methylethylketone were placed in a reaction vessel and the reaction mixtures were stirred by heating at 50° C. under a nitrogen current. 15.42 g (0.14 mole) of resorcinol, 32 g of pyridine, and 100 g of methylethylketone were added dropwise to the above reaction vessel using a dropping funnel. After the completion of the addition, the reaction solution was refluxed with stirring under a nitrogen current for 2 hours. After the reaction, the precipitate was separated by filtration and the filtrated solid was washed by water and dried. 64 g of white colored crystals (1,3-bis(4-nitrocinnamic acid) benzene) was yielded.

(2) Synthesis of 1,3-bis(4-aminocinnamic acid) benzene 10.13 g (22 milimole) of 1,3-bis(4-nitrocinnamic acid), 0.5 g of carbon black containing 5% Pt (product with water content of approximately 50%), and 100 ml of 1, 4-dioxane were placed in a reaction vessel (hydrogenating apparatus), and then the reaction mixtures were heated at 60° C. with stirring under a hydrogen atmosphere. 3.14 L of hydrogen was absorbed in approximately 4 hours, and the reaction was completed when the absorption of hydrogen stopped. Then the reacted solution was filtered for removing carbon containing Pt and the filtrate was concentrated and recrystallized. 8.0 g of 1,3-bis(4-aminocinnamic acid) benzene was yielded. The exothermic peak temperature was 231° C.

(3) Synthesis of polyimide 40.0 g (0.1 mole) of 1,3-bis(4-aminocinnamic acid) benzene and 300 g of DMAc were placed in a 2,000 ml-separable flask equipped with a stirrer. 44.4 g (0.1 mole) of 6FDA was added while vigorously stirring and the stirring was continued for 30 minutes. For imidization, 9.3 g (0.2 mole) of β-picoline, 50 g of acetic anhydride, and 100 g of DMAc were added to the above reaction solution, and then heated at approximately 150° C. Such reaction was performed under a nitrogen current. After the completion of the reaction, the reacted solution was poured into methanol, and the precipitate was separated by filtration and dried. 79 g of polyimide was yielded as white powder. The weight-average molecular weight of the polyimide powder was 100,000.

Example 9

(1) Synthesis of 1,2-ethane-bis(4-nitrocinnamate)

11.64 g (55 milimole) of 4-nitrocinnamoyl chloride obtained in Example 2, 100 ml of o-dichlorobenzene, and 1.55 g (25 milimole) of ethylene glycol were placed in a reaction vessel and the reaction mixtures were stirred by heating in the range of 120 to 130° C. under a nitrogen current. Approximately 2 hours later, the reacted solution was poured into methanol. A 6.83-g white colored solid (1,2-ethane-bis(4-nitrocinnamate) was yielded. The precipitate was separated by filtration and dried.

(2) Synthesis of 1,2-ethane-bis(4-aminocinnamate)

9.07 g (22 milimole) of 1,3-ethane-bis(4-nitrocinnamate), 0.5 g of carbon black containing 5% Pt (product with water content of approximately 50%), and 100 ml of 1, 4-dioxane were placed in a reaction vessel (hydrogenating apparatus), and then the reaction mixtures were heated at 60° C. with stirring under a hydrogen atmosphere. 3.18 L of hydrogen was absorbed in approximately 4 hours, and the reaction was completed when the absorption of hydrogen stopped. Then the reacted solution was filtered for removing carbon containing Pt, concentrated, and recrystallized. 7.0 g of 1,2-etane-bis(4-aminocinnamate) was yielded. The exothermic peak temperature was 231° C.

(3) Synthesis of polyimide 35.2 g (0.1 mole) of 1,3-bis(4-aminocinnamic acid) ethyl and 300 g of DMAc were placed in a 2,000 ml-separable flask equipped with a stirrer. 44.4 g (0.1 mole) of 6FDA was added while vigorously stirring and stirring was continued for 30 minutes. For imidization, 9.3 g (0.2 mole) of 13β-picoline, 50 g of acetic anhydride, and 100 g of DMAc were added to the above reaction solution, and then the reaction solution was heated at approximately 150° C. Such reaction was performed under a nitrogen current. After the completion of the reaction, the reacted solution was poured into methanol, and the precipitate was separated by filtration and dried. 74 g of polyimide was yielded as white powder. The weight-average molecular weight of the polyimide powder was 100,000.

In Example 10, polyimide was obtained by reaction between diol-terminated imido oligomer and chloride of cinnamic acid derivative.

Example 10

(1) Synthesis of diol-terminated imido oligomer and 2-carboxychloro-cinnamoyl chloride 115.3 g (0.2 mole) of ESDA was placed in a 1,000 ml-round bottom flask equipped with a stirrer and a dean stark tube. 30.7 g (0.48 mole) of 2-aminoethanol and 200 g of DMAc were added while vigorously stirring and the stirring was continued for 30 minutes. 41.9 g (0.45 mole) of β-picoline and 50 g of toluene were added to the above reaction solution, and then the reaction solution was refluxed with dehydrating through the dean stark tube for imidization (approximately 4 hours). After the completion of the reaction, the reactant was free of solvent. 138 g of diol-terminated imido oligomer was obtained and purified by column purification (silica gel/solvent:acetone). 80 g of diol-terminated Imido oligomer was yielded. 28.8 g (0.15 mole) of 2-carboxy cinnamic acid and 300 g of ethyl acetate were placed in a reaction vessel. While 90 g of thionyl chloride with some drops of DMF was dropped into the reaction solution, the reaction solution was refluxed with stirring until the generation of hydrogen chloride gas stopped. The reacted solution was concentrated until a solid could be precipitated, and was poured into hexane. The precipitate was separated by filtration, and dried. 25.9 g of dichloride of 2-carboxycinnamic acid was yielded.

(2) Synthesis of polyimide 11.4 g (50 milimole) of 100 ml of 2-carboxychloro-cinnamoylchrolide, 200 ml of nitrobenzene, and 33.1 g (50 milimole) of diol-terminated imido oligomer were placed in a reaction vessel and the reaction mixture was heated in the range of 120 to 130° C. with stirring under a nitrogen current. About 2 hours later, the reacted solution was poured into methanol, and the precipitate was separated by filtration and dried. A 33.6 g-white colored solid was yielded. The weight-average molecular weight of the polyimide powder was 80,000.

In the following Examples 11 through 13, a novel acid dianhydride having cinnamoyl group according to the present invention was manufactured to synthesize a polyimide composition.

Example 11

(1) Synthesis of 2-carboxychloro-cinnamoylchrolide 28.8 g (0.15 mole) of 2-carboxycinnamic acid and 300 g of ethyl acetate were placed in a reaction vessel. While 90 g of thionyl chloride with some drops of DMF was dropped into the reactor vessel, the reaction vessel was refluxed with stirring until the generation of hydrogen chloride gas stopped. The reacted solution was concentrated until a solid could be precipitated. The reacted solution was poured into hexane and the precipitated solid was separated by filtration and dried. 25.9 g of chloride of 2-carboxycinnamic acid was yielded.

(2) Synthesis of acid dianhydride by reaction of 2-carboxychloro-cinnamoylchrolide-and 3-hydroxyphthalic anhydride 4.92 g (30 milimole) of 3-hydroxyphthalic anhydride, 50 g of methylethylketone, and 3 g of pyridine were placed in a reaction vessel and the reaction mixtures were heated at 60° C. with stirring under a nitrogen current. 3.44 g (15 milimole) of 2-carboxychloro-cinnamoylchrolide was dissolved in 30 g of methylethylketone and slowly added dropwise to the solution. After the completion of the addition, stirring was continued for approximately 2 hours. After cooling, a precipitated solid was separated by filtration. Then the solid was filtrated, washed with water, and recrystallized in acetic anhydride. 5.5 g of acid dianhydride was yielded. The exothermic peak temperature was 233° C.

(3) Synthesis of polyimide 2.00 g (0.01 mole) of oxidianiline and 30 g of DMAc were placed in a 300 ml-separable flask equipped with a stirrer. 4.84 g (0.01 mole) of acid dianhydride obtained in Example 1 was added while vigorously stirring and the stirring was continued for 30 minutes. For imidization, 0.93 g (0.02 mole) of β-picoline, 5 g of acetic anhydride, and 10 g of DMAc were added to the above reaction solution, and the reaction solution was heated at approximately 120° C. Such reaction was performed under a nitrogen current. After the completion of the reaction, the reacted solution was poured into methanol, separated by filtration, and dried. 6.2 g of polyimide was yielded as yellow powder. The weight-average molecular weight of the polyimide powder was 80,000.

Example 12

(1) Synthesis of diol by Reaction of ethylene glycol and 2-carboxychloro-cinnamoylchrolide 186.2 g (3 moles) of ethylene glycol and 22.9 g (0.1 mole) of 2-carboxychloro-cinnamoylchrolide were placed in a reaction vessel and the reaction mixtures were heated at approximately 120° C. for approximately 2 hours with stirring under a nitrogen current until the generation of hydrogen chloride stopped.

After the completion of the reaction, the reacted solution was poured into water. This aqueous phase was extracted with methylene chloride, concentrated, and dried. 25 g of diol was yielded.

(2) Synthesis of Acid dianhydride by Reaction of the Above diol and trimellitic chloride 16.3 g (58 milimole) of the above diol, 25.3 g (120 milimole) of trimellitic chloride, and 450 ml of nitrobenzene were placed in a reaction vessel. The reaction mixtures were heated at approximately 120° C. with stirring under a nitrogen current for approximately 2 hours until the generation of hydrogen chloride stopped. After cooling, the reacted solution was poured into hexane. The separated solution was divided, and dried under reduced pressure, and purified by column purification. 19 g of acid dianhydride was yielded. The exothermic peak temperature was 232° C.

(3) Synthesis of polyimide 2.00 g (0.01 mole) of oxidianiline and 30 g of DMAc were placed in a 300 ml-separable flask equipped with a stirrer. 6.29 g (0.01 mole) of acid dianhydride obtained in Example 2 was added while vigorously stirring and the stirring was continued for 30 minutes. For imidization, 0.93 g (0.02 mole) of β-picoline, 5 g of acetic anhydride, and 10 g of DMAc were added to the above reaction solution, and heated at approximately 120° C. Such reaction was performed under a nitrogen current. After the completion of the reaction, the reacted solution was poured into methanol, and separated by filtration and dried. 7.7 g of polyimide was yielded as yellow powder. The weight-average molecular weight of the polyimide powder was 90,000.

Example 13

(1) Synthesis of diol by Reaction of glycerol and cinnamoyl chloride 46.04 g (0.5 mole) of glycerol and 8.33 g (0.05 mole) of cinnamoyl chloride were placed in a reaction vessel and the reaction mixtures were heated at approximately 120° C. for approximately 2 hours with stirring under a nitrogen current until the generation of hydrogen chloride stopped.

After the completion of the reaction, the reacted solution was poured into water. The reactant was extracted with dichloromethane, dried, and purified by column chromatography. 9.9 g of mixture of 2-(1,3-propyleneglycol)cinnamate and 3-(1, 2-propyleneglycol)cinnamate (a mixture of approximately the ratio of 3:1) was yielded. This mixture was identified with a heavy hydrogen acetone, using H-NMAR spectrometer.

(2) Synthesis of acid dianhydride by reaction of the above mixture of diol and trimellitic chloride 8.89 g (40 milimole) of the above diol, 17.9 g (85 milimole) of trimellitic anhydride chloride, and 150 ml of o-dichlorobenzene were placed in a reaction vessel. The reaction mixtures were heated at approximately 120° C. with stirring under a nitrogen current until the generation of hydrogen chloride stopped (for approximately 3 hours). After cooling, the reaction solution was poured into hexane and dried under reduced pressure, and purified by column chromatography. 8.3 g of desired acid anhydride was yielded. The exothermic peak temperature was 235° C.

(3) Synthesis of polyimide 2.00 g (0.01 mole) of oxidianiline and 30 g of DMAc were placed in a 300 ml-separable flask equipped with a stirrer. 5.70 g (0.01 mole) of acid dianhydride obtained in Example 3 was added while vigorously stirring and the reaction mixtures were continuously stirred for 30 minutes. For imidization, 0.93 g (0.02 mole) of β-picoline, 5 g of acetic anhydride, and 10 g of DMAc were added to the above reacted solution, and the reaction solution was heated at approximately 120° C. Such reaction was performed under a nitrogen current. After the completion of the reaction, the reacted solution was poured into methanol, and the precipitate was separated by filtration and dried. 7.2 g of polyimide was yielded as yellow powder. The weight-average molecular weight of the polyimide powder was 80,000.

Example 14

9.01 g (0.1 mole) of 1,3-diamino-propane-2-ol and 100 g of DMAc were placed in a 1,000 ml-separable flask equipped with a stirrer and a dean stark tube. 44.4 g (0.1 mole) of 6FDA was added while vigorously stirring and the stirring was continued for 30 minutes. For imidization, 18.6 g of β-picoline and 50 g of toluene were added to the above reaction solution, and the reaction solution was refluxed for approximately 3 hours with stirring and aggressively dehydrating. Such reaction was performed under a nitrogen current. After the completion of the reaction, the reacted solution was poured into methanol, separated by filtration and dried. 48 g of polyimide was yielded as white powder. 25 g of this white polyimide powder, 200 ml of nitrobenzene, and 16.6 g (0.1 mole) of cinnamoyl chloride were placed in a reaction vessel. Then the reaction solution was heated at approximately 120° C. for 2 hours with stirring. The reacted solution was poured into methanol, and separated by filtration and dried. 31 g of polyimide was yielded as white powder containing cinnamoyl group in a side chain. The weight-average molecular weight of the polyimide powder was 70,000.

Example 15

(1) Synthesis of 1, 3-bis(4-nitrophenoxy)-2-propylalcohol 76.5 g (0.55 mole) of p-nitrophenol, 32.3 g (0.25 mole) of glycerol-αα'-dichlorohydrin, and 500 ml of xylene were added to a reaction solution, and the reaction mixtures were heated with stirring under a nitrogen current. After dissolving the solid, 345 g (2.5 moles) of potassium carbonate anhydride was added, and the reaction mixtures were refluxed with stirring for 12 hours. The reacted solution was separated by filtration while it was warm. After cooling, hexane was added to the filtrate. A yellow viscous liquid was obtained. After column purification and drying this liquid, a 55 g-yellow viscous liquid (1,3-bis(4-nitrophenoxy)-2-propyl alcohol) was obtained.

(2) Synthesis of 1,3-bis(4-nitrophenoxy)-2-propyl cinnamate 33.4 g (0.1 mole) of the above viscous liquid, 25 g (0.15 mole) of cinnamoyl chloride, and 300 ml of o-dichlorobenzene were placed in a reaction vessel and the reaction mixtures were heated at approximately 120° C. for 2 hours with stirring. Hexane was added to the reaction solution. A yellow viscous liquid was obtained. After column purification and drying the liquid, a 3.5 g-yellow viscous liquid (1,3-bis(4-nitrophenoxy)-2-propyl cinnamate) was obtained.

(3) Synthesis of 1,3-bis(4-aminophenoxy)-2-propyl cinnamate 34.8 g (0.075 mole) of 1,3-bis(4-nitrophenoxy)-2-propyl cinnamate, 15 g of carbon black containing 5% Pt and 2% iron (product with water content of approximately 50%), and 300 ml of 1,4-dioxane were placed in a reaction vessel (hydrogenating apparatus). And stirring was conducted by heating at 60° C. under a hydrogen atmosphere. In approximately 8 hours, 10.8 L of hydrogen was absorbed and the reaction was completed when the absorption of hydrogen stopped. Then the reacted solution was separated by filtration for removing the catalyst and the filtrate was concentrated. 30.3 g of 1,3-bis(4-aminophenoxy)-2-propyl cinnamate was yielded. The exothermic peak temperature was 230° C.

(4) Synthesis of polyimide 30.3 g (0.075 mole) of 1,3-bis(4-aminophenoxy)-2-propyl cinnamate and 250 g of DMAc were placed in a 2,000 ml-separable flask equipped with a stirrer. 33.3 g (0.075 mole) of 6FDA was added while vigorously stirring and the stirring was continued for 30 minutes. For imidization, 9.3 g (0.2 mole) of β-picoline, 50 g of acetic anhydride, and 100 g of DMAc were added to the above reaction solution, and the reaction solution was heated at approximately 120° C. Such reaction was performed under a nitrogen current. After the completion of the reaction, the reacted solution was poured into methanol, and separated by filtration and dried. 60 g of polyimide was yielded as white powder. The weight-average molecular weight of this polyimide powder was 120,000.

Example 16

(1) Synthesis of 1,3-bis(4-aminophenoxy)-2-propylalcohol

A 33.4 g (0.1 mole)-viscous liquid of 1,3-bis(4-nitrophenoxy)-2-propyl alcohol obtained in Example 6, 3 g of activated charcoal powder containing 5% Pd, and 250 ml of 1,4-dioxane were placed in a reaction vessel (hydrogenating apparatus). And the reaction mixtures were heated at 60° C. under a hydrogen atmosphere. In approximately 8 hours, 14.4 L of hydrogen was absorbed and the reaction was completed when the absorption of hydrogen stopped. Then the reacted solution was separated by filtration and the filtrate was concentrated for removing the catalyst. 27.4 g of 1,3-bis(4- aminophenoxy)-2-propyl alcohol was obtained.

(2) Synthesis of polyimide 27.4 g (0.1 mole) of 1,3-bis(4-aminophenoxy)2-propylalcohol and 250 g of DMAc were placed in a 2,000 ml-separable flask equipped with a stirrer. 44.4 g (0.1 mole) of 6FDA was added while vigorously stirring and the stirring was continued for 30 minutes. For imidization, 18.6 g of β-picoline and 50 g of toluene were added to the above reaction solution, and the reaction solution was refluxed for approximately 3 hours with stirring and aggressively dehydrating. Such reaction was performed under a nitrogen current. After the completion of the reaction, the reacted solution was poured into methanol, and separated by filtration and dried. 67 g of polyimide was yielded as white powder.

(3) Introduction of cinnamoyl Group into a Side Chain of polyimide 34.1 g of the white powder of polyimide obtained in the above Example 14–Example 16, 350 ml of nitrobenzene, and 16.6 g (0.1 mole) of cinnamoyl chloride were placed in a reaction vessel. Then the reaction mixtures were heated at approximately 120° C. for 4 hours with stirring. The reacted solution was poured into methanol, 40 g of polyimide was yielded as white powder by separating the solution and the precipitate was filtered and dried. The polyimide containing cinnamoyl group in a side chain thereof was yielded in white powder, which is corresponding to polyimide obtained in Example 14–Example 16. The weight-average molecular weight of the polyimide powder was 65,000.

INDUSTRIAL APPLICABILITY

The present invention can provide novel polyimide compositions which include a cinnamoyl group or a derived cinnamoyl group. These novel polyimide compositions according to the present invention contribute to the printing field, such as etching processing and resin letterpress, as excellent photosensitive resin, electronics parts uses, such as fine pattern for a semiconductor device, forming a resist layer of a printed circuit board, and an interlayer insulating layer of a semiconductor device, and expand various uses such as materials for forming an optical disk substrate, or the like.

What is claimed is:

1. A novel polyimide composition comprising a polyimide which comprises a monomer unit represented by the general formula (1) in a proportion of not smaller than 1% by weight:

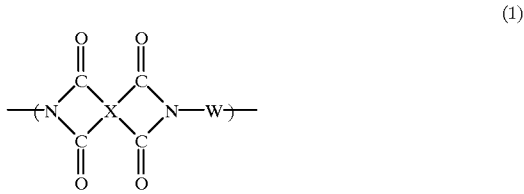

wherein X is a tetravalent organic group, and W is at least one divalent organic group selected from divalent organic groups represented by the formulae:

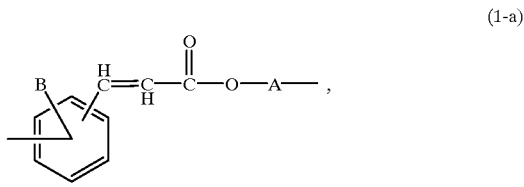

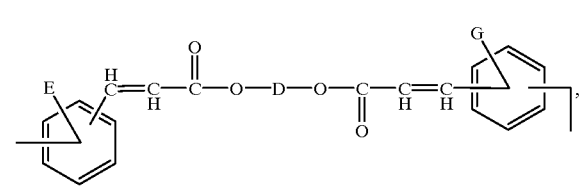

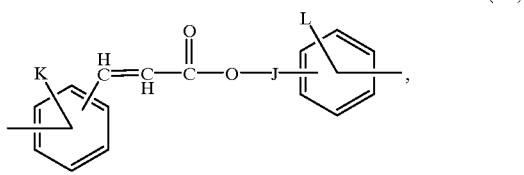

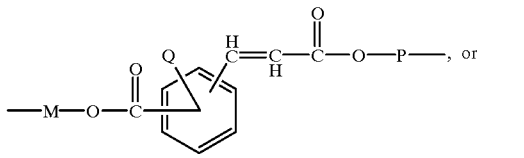

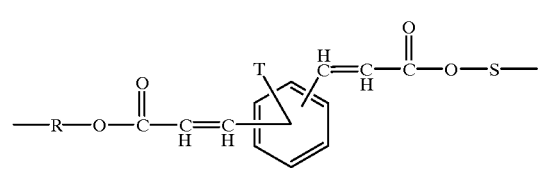

wherein A represents a divalent organic group, B represents H, $CH_3$, F, Cl, Br or $CH_3O$—, D represents a divalent organic group, E represents H, $CH_3$, F, Cl, Br, or $CH_3O$—, G represents H, $CH_3$, F, Cl, Br, or $CH_3O$—, J represents —$CH_2$—, —$(CH_2)_m$—O—, or —$(CH_2)_n$—OCO— wherein m=1 to 15 and n=1 to 15, K represents H, $CH_3$, F, Cl, Br, or CH₃O—, L represents H, CH₃, F, Cl, Br, or CH₃O—, M and P may be the same or different and each represents a divalent organic group, R and S may be the same or different and each represents a divalent organic group, and T represents H, CH₃, F, Cl, Br, or CH₃O—.

2. The novel polyimide composition of claim 1, wherein X in said general formula (1) represents one or two or more kinds of tetravalent organic groups which each comprise one to three aromatic rings or an aliphatic ring.

3. The novel polyimide composition according to claim 1, wherein W is represented by formula (1-a) in which A is a divalent organic group selected from the following groups:

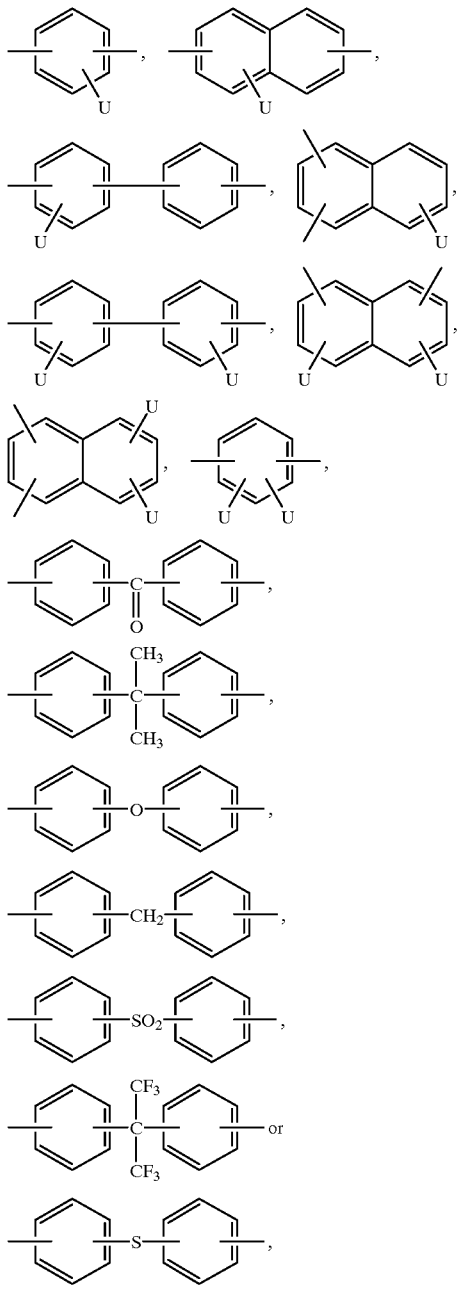

wherein U represents H, CH₃, F, Cl, Br, or CH₃O—.

4. The novel polyimide composition according to claim 1, wherein W is represented by formula (1-b) in which D is a divalent organic group selected from the following groups:

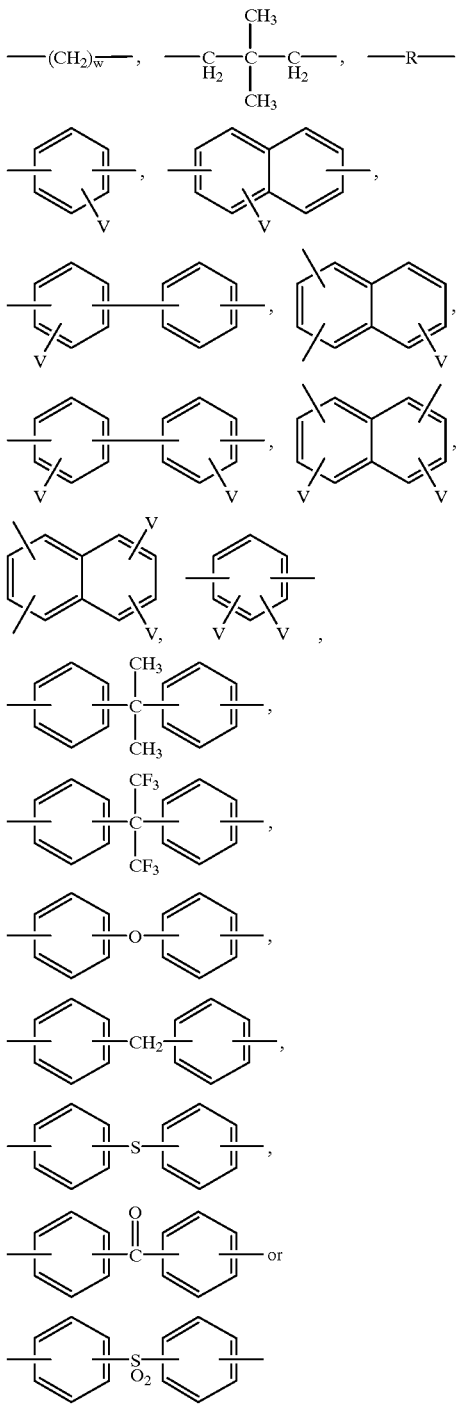

wherein w is an integer from 1 to 40, and V represents H, CH₃, F, Cl, Br, or CH₃O—.

5. The novel polyimide composition according to claim 1, wherein W is represented by formula (1-c).

6. The novel polyimide composition according to claim 1, wherein W is represented by formula (1-d) in which M and P may be the same or different and each represents a divalent organic group selected from the following groups:

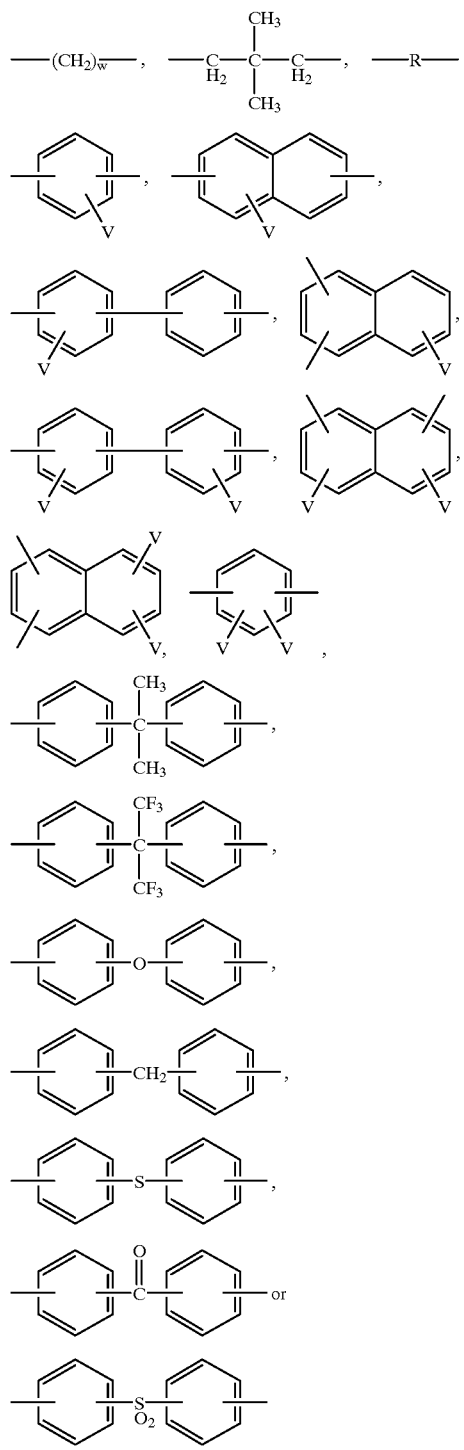

wherein w is an integer from 1 to 40, and Q and V each represent H, CH$_3$, F, Cl, Br, or CH$_3$O—.

7. The novel polyimide composition according to claim 1, wherein W is represented by formula (1-e) in which R and S, which may be the same or different, each represents a divalent organic group selected from the following groups:

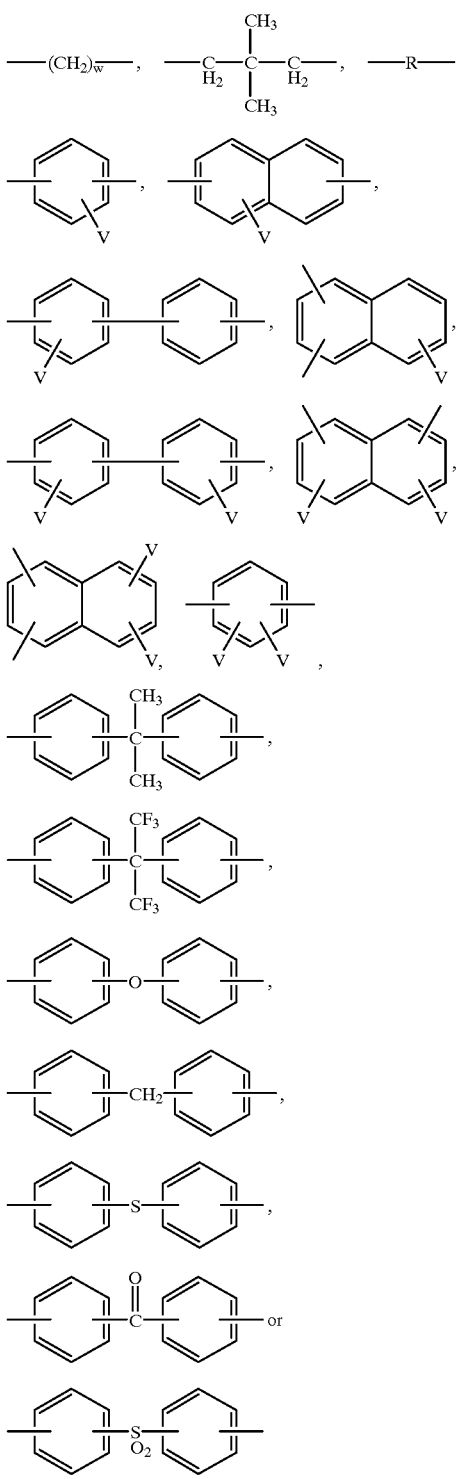

wherein w is an integer from 1 to 40, and Q and V and each represent H, CH$_3$, F, Cl, Br, or CH$_3$O—.

8. A novel polyimide composition comprising a polyimide which comprises a monomer unit represented by general formula (1) in a proportion of not smaller than 1% by weight

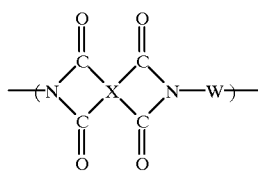

wherein X is a tetravalent organic group and W is represented by formula (1-f):

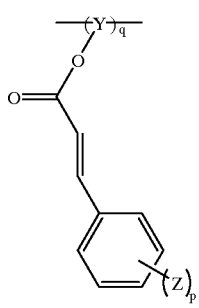

wherein Z represents H, CH$_3$, F, Cl, Br, or CH$_3$O—, p=1 to 3, q=1 to 3, and Y is a trivalent organic group selected from the following groups:

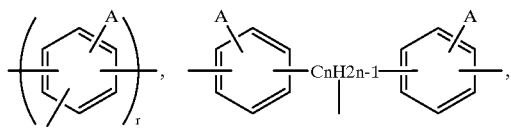

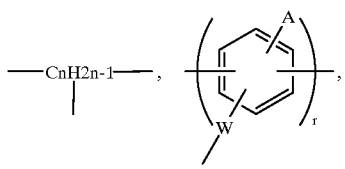

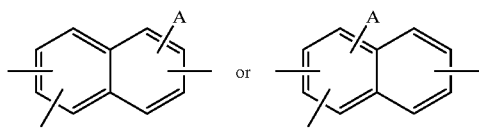

wherein A represents H, CH$_3$, F, Cl, Br, or CH$_3$O—, r=1 to 3, n=1 to 2, and W represents a divalent organic group selected from —CH$_2$—, —(CH$_2$)$_m$—O—, or —(CH$_2$)$_k$—OCO—, wherein m=1 to 15, k=1 to 20 (k≠2).

9. The novel polyimide composition of claim 8, wherein X in said general formula represents one or two or more kinds of tetravalent organic groups which each comprise one to three aromatic rings or an aliphatic ring.

10. A novel polyimide composition comprising a polyimide which comprises a monomer unit represented by the general formula (2) in a proportion of not smaller than 1% by weight:

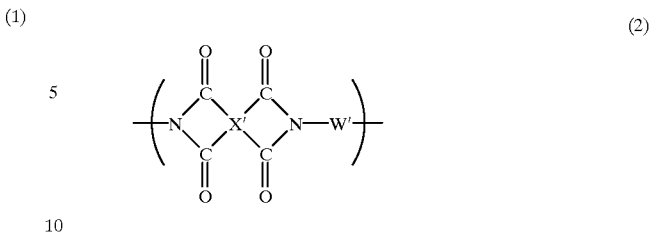

wherein X' is a group represented by the formula (2-a):

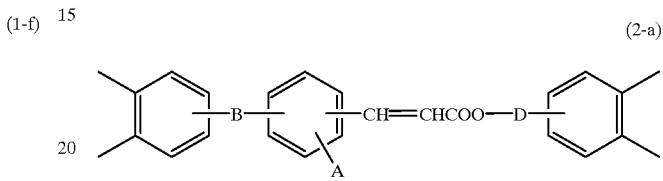

B represents a divalent organic group, D represents a single bond (—) or a divalent organic group, A represents H, CH$_3$, F, Cl, Br, or CH$_3$O—; and W' represents a divalent organic group.

11. The novel polyimide composition according to claim 10, wherein B represents a divalent organic group selected from the group consisting of —COO—, OCO—, —O—, —O—E—O—, —COO—E—OCO—, —O—E—OCO—, —O—E—COO—, and —OOCCH=CH—, and E represents —C$_m$H$_{2m}$— wherein m represents an integer from 1 to 20, a benzene ring, a naphthalene ring, or a biphenyl group.

12. The novel polyimide composition according to claim 10, wherein D represents a divalent organic group selected from among —F—OCO— or —F—O—, and F represents —C$_m$H$_2$—, wherein m represents an integer from 1 to 20, a benzene ring, or a naphthalene ring.

13. The novel polyimide composition according to claim 10, wherein D represents a single bond.

14. A novel polyimide composition comprising a polyimide which comprises a monomer unit represented by the general formula (2) in a proportion of not smaller than 1% by weight:

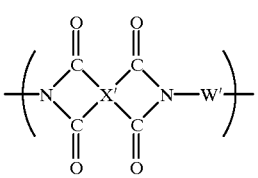

wherein X' is a group represented by formula (2-b):

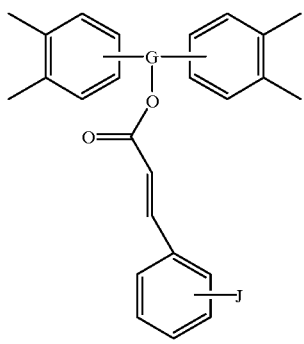

(2-b)

wherein G is a trivalent group selected from the following groups:

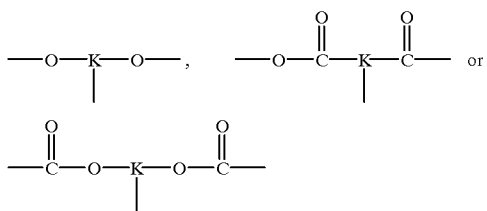

or

K represents $C_nH_{2n-1}$ and n represents an integer of 1–20, a benzene ring, a naphthalene ring, or a biphenyl, J represents H, $CH_3$, F, Cl, Br, or $CH_3O$, and W' represents a divalent organic group.

15. A method of the producing polyimide composition comprising a monomer unit of the general formula (1)

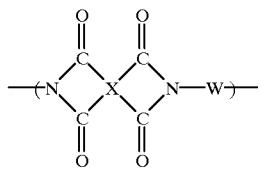

(1)

wherein X is a tetravalent organic group, and W is represented by formula (1-f)

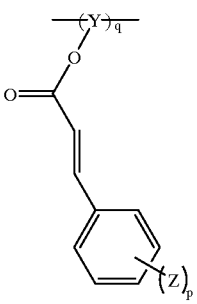

(1-f)

mixing at least one acid dianhydride and at least one diamine which comprises a diamine represented by the general formula (8)

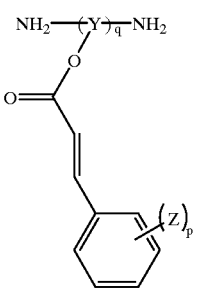

(8)

wherein Y represents a trivalent organic group, Z represents H, $CH_3$, F, Cl, Br or $CH_3O$—, p=1 to 3, and q=1 to 3 to obtain a polyamic acid; and imidizing said polyamic acid.

* * * * *